US007112405B2

(12) United States Patent
Kmiec et al.

(10) Patent No.: US 7,112,405 B2
(45) Date of Patent: Sep. 26, 2006

(54) COMPOSITIONS AND METHODS FOR ENHANCING OLIGONUCLEOTIDE-MEDIATED GENE ALTERATION

(75) Inventors: Eric B. Kmiec, Landenberg, PA (US); Michael C. Rice, Newtown, PA (US); Li Liu, Newark, DE (US)

(73) Assignee: University of Delaware, Wilmington, DE (US)

( * ) Notice: Subject to any disclaimer, the term of this patent is extended or adjusted under 35 U.S.C. 154(b) by 495 days.

(21) Appl. No.: 10/260,375

(22) Filed: Sep. 27, 2002

(65) Prior Publication Data

US 2003/0199091 A1 Oct. 23, 2003

Related U.S. Application Data

(60) Provisional application No. 60/337,129, filed on Dec. 4, 2001, provisional application No. 60/326,041, filed on Sep. 27, 2001, provisional application No. 60/393,330, filed on Jul. 1, 2002.

(51) Int. Cl.
C12Q 1/68 (2006.01)
G01N 33/53 (2006.01)
(52) U.S. Cl. ............................. 435/6; 435/7.1
(58) Field of Classification Search .................. 435/6, 435/7.1
See application file for complete search history.

(56) References Cited

U.S. PATENT DOCUMENTS

| 5,139,941 | A | 8/1992 | Muzyczka et al. |
| 5,565,350 | A | 10/1996 | Kmiec |
| 5,700,470 | A | 12/1997 | Saito et al. |
| 5,731,181 | A | 3/1998 | Kmiec |
| 5,795,972 | A | 8/1998 | Kmiec |
| 5,801,154 | A | 9/1998 | Baracchini |
| 5,871,984 | A | 2/1999 | Kmiec |
| 5,912,340 | A | 6/1999 | Kutyavin |
| 5,928,638 | A | 7/1999 | Uchida et al. |
| 5,945,339 | A | 8/1999 | Holloman |
| 5,955,363 | A | 9/1999 | Lewis |
| 6,004,804 | A | 12/1999 | Kumar |
| 6,136,601 | A | 10/2000 | Meyer |
| 6,261,841 | B1 | 7/2001 | Cohen et al. |
| 6,271,360 | B1 | 8/2001 | Metz |
| 6,391,564 | B1 * | 5/2002 | Haaf et al. .................. 435/7.1 |
| 2002/0119570 | A1 | 8/2002 | Yoon |
| 2003/0051270 | A1 | 3/2003 | Kmiec et al. |
| 2003/0217377 | A1 | 11/2003 | Kmiec et al. |

FOREIGN PATENT DOCUMENTS

| WO | WO 90/12084 | 10/1990 |
| WO | WO 99/14226 | 3/1999 |
| WO | WO 99/32619 | 7/1999 |
| WO | WO 99/58702 | 11/1999 |
| WO | WO 00/56748 | 9/2000 |
| WO | WO 00/63397 | 10/2000 |
| WO | WO 00/66604 | 11/2000 |
| WO | WO 01/15740 | 3/2001 |
| WO | WO 01/24615 | 4/2001 |
| WO | WO 01/68836 | 9/2001 |
| WO | WO 01/73002 | 10/2001 |
| WO | WO 01/92512 | 12/2001 |
| WO | WO 02/10364 | 2/2002 |
| WO | WO 02/26967 | 4/2002 |

OTHER PUBLICATIONS

Baumann et al. Role of the Human RAD51 Protein in Homologous Recombination and Double Strande-Break Repair, TIBS, 1998, vol. 23, p. 247-251.*
Alber et al., "Nucleotide Sequence of the Triose Phosphate Isomerase Gene of *Saccharomyces cerevisiae*", *J. Mol. Appl. Genet* 1:419-34 (1982).
Alexeev et al., "Stable and inheritable changes in genotype and phenotype of albino melanocytes induced by an RNA-DNA oligonucleotide," *Nature Biotech.* 16:1343-1346 (1998).
Blau, "Current Status of stem cell therapy and prospects for gene therapy for the disorders of globin synthesis", *Bailliers Clin. Haematol* 11:257-275 (1998).
Blouin et al., "Altered Hematopoiesis in Murine Sickle Cell Disease", *Blood* 94:1451-1459 (1999).
Campbell et al., "Homologous recombination involving small single-stranded oligonucleotides in human cells," *New Biologist* 1:223-227 (1989).
Chan et al., "Targeted correction of an episomal gene in mammalian cells by a short DNA fragment tethered to a triplex-forming oligonucleotide," *J. Biol. Chem.* 274:11541-11548 (1999).
Chan et al., "Triplex DNA: fundamentals, advances, and potential applications for gene therapy," *J. Mol. Med.* 75:267-282 (1997).
Cole-Strauss et al., "Correction of the mutation responsible for sickle cell anemia by an RNA-DNA oligonucleotide," *Science* 273:1386-1389 (1996).
Crystal, Ronald G., "Transfer of Genes to Humans: Early Lessons and Obstacles to Success," *Science* 270: 404-410 (1995).
Culver et al., "Correction of chromosomal point mutations in human cells with bifunctional oligonucleotides," *Nat. Biotechnol.* 17:989-993 (1999).
Fabry et al., "Second generation knockout sickle mice: the effect of HbF", *Blood* 97:410-418 (2001).

(Continued)

Primary Examiner—Kenneth R. Horlick
Assistant Examiner—Joyce Tung
(74) Attorney, Agent, or Firm—McCarter & English, LLP

(57) ABSTRACT

Composition and methods for enhancing oligonucleotide-directed nucleic acid sequence alteration in vivo, ex vivo and in vitro are presented. These methods and compositions involve cells and cell-free extracts with altered levels or activities of a protein from the RAD52 epistasis group, the mismatch repair group and/or the excision repair group.

10 Claims, 9 Drawing Sheets

OTHER PUBLICATIONS

Gamper et al., "A plausible mechanism for gene correction by chimeric oligonucleotides," *Biochemistry* 39(19): 5808-16 (2000).

Gamper et al., "The DNA strand of chimeric RNA/DNA oligonucleotides can direct gene repair/conversion activity in mammalian and plant cell-free extracts," *Nucleic Acids Res.* 28:4332-4339 (2000).

Helene, et al., "The anti-gene strategy: control of gene expression by triplex-forming-oligonucleotides" *Anticancer Drug Des.* 6(6):569-84 (1991).

Helene et al., "Control of Gene Expression by Triple Helix-Forming Oligonucleotides", *Ann. N. Y. Acad. Sci.* 660:27-36 (1992).

Heyer, "The search for the right partner: Homologous pairing and DNA strand exchange proteins in eukaryotes", *Experientia* 50(3):223-233 (1994).

Igoucheva et al., "Targeted gene correction by small single-stranded oligonucleotides in mammalian cells, " *Gene Therapy* 8:391-399 (2001).

Kaji et al., "Gene and Stem Cell Therapies," *JAMA* 285(5): 545-550 (2001).

Kmiec et al., "Targeted gene repair in mammalian cells using chimeric RNA/DNA oligonucleotides," *Cold Spring Harbor Monograph Series* 36: 643-670 (1999).

Kren et al., "Correction of the UDP-glucuronosyltransferase gene defect in the Gunn rat model of Crigler-Najjar syndrome type I with a chimeric oligonucleotide," *Proc. Natl. Acad. Sci. USA* 96:10349-10354 (1999).

Kunzelmann et al., "Gene targeting of CFTR DNA in CF epithelial cells," *Gene Ther.* 3:859-867 (1996).

Liu et al., "In vivo gene repair of point and frameshift mutations directed by chimeric RNA/DNA oligonucleotides and modified single-stranded oligonucleotides," *Nucl. Acids Res.* 29(20): 4238-50 (2001).

Maher, "DNA Triple-Helix Formation: An Approach to Artificial Gene Repressors", *Bioessays* 14(12):807-15 (1992).

Moerschell et al., "Transformation of yeast with synthetic oligonucleotides," *Proc. Natl. Acad. Sci. USA* 85:524-528 (1988).

Ørum et al., "Detection of the factor V Leiden mutation by direct allele-specific hybridization of PCR amplicons to photoimmobilized locked nucleic acids," *Clinical Chemistry* 45(11): 1898-1905 (1999).

Paques et al., "Multiple Pathways of Recombination Induced by Double-Strand Breaks in *Saccharomyces cerevisiae*", *Microbiol. and Molec. Biol. Rev.* 63(2):349-404 (1999).

Rando et al., "Rescue of dystrophin expression in *mdx* mouse muscle by RNA/DNA oligonucleotides," *Proc. Natl. Acad. Sci. USA* 97:5363-5368 (2000).

Rice et al., "The potential of nucleic acid repair in functional genomics," *Nature Biotech.* 19(4): 321-26 (2001).

Santisteban et al., "Three new adenosine deaminase mutations that define a splicing enhancer and cause severe and partial phenotypes: Implications for evolution of a CpG hotspot and expression of a transduced ADA cDNA," *Human Molec. Genetics* 4(11): 2081-87 (1995).

Sayers et al., "5'-3' Exonucleases in Phosphorothioate-based Oligonucleotide-directed Mutagenesis," *Nucleic Acids Research* 16(3): 791-801 (1988).

Spangrude et al., "Purification and Characterization of Mouse Hematopoietic Stem Cells", *Science* 214:58-62 (1988).

Thacker et al., "A surfeit of RAD51-like genes?" *Trends Genet.* 15: 166-68 (1999).

Thompson et al., "Homologous recombinatorial repair of DNA ensures mammalian chromosome stability", *Mutations Res.* 477:131-153 (2001).

Vasquez et al., "Chromosomal mutations induced by triplex-forming oligonucleotides in mammalian cells," *Nucl. Acids Res.* 27:1176-1181 (1999).

Vasquez et al., "Specific mutations induced by triplex-forming oligonucleotides in mice," *Science* 290:530-532 (2000).

Verma et al., "Gene Therapy- Promises, Problems, and Prospects," *Nature* 389: 239-242 (1997).

Weiss et al., "Molecular cloning and characterization of the yeast RAD10 gene and expression of RAD10 protein in *E. coli*," *The EMBO Journal* 4(6): 1575-1582 (1985).

Woolf et al., "Toward the therapeutic editing of mutated RNA sequences," *Proc. Natl. Acad. Sci. USA* 92: 8298-8302 (1995).

Xu et al., "Activation of human γ-globin gene expression via triplex-forming oligonucleotide (TFO)-directed mutations in the γ-globin gene 5' flanking region," *Gene* 242:219-228 (2000).

Yamamoto et al., "Strand-specificity in the transformation of yeast with synthetic oligonucleotides," *Genetics* 131:811-819 (1992).

Yanez et al., "Therapeutic gene targeting," *Gene Therapy* 5:149-159 (1998).

\* cited by examiner

KanGG

HygE3T/25:    5'-AGG GCG TGG ATA CGT CCT GCG GGT A-3'

HygE3T/74:    5'-CTC GTG CTT TCA GCT TCG ATG TAG GAG GGC
              GTG GAT ACG TCC TGC GGG TAA ATA GCT GCG
              CCG ATG GTT TCT AC-3'

HygE3T/74α:   5'-GTA GAA ACC ATC GGC GCA GCT ATT TAC CCG
              CAG GAC GTA TCC ACG CCC TCC TAC ATC GAA
              GCT GAA AGC ACG AG-3'

HygGG/Rev:

Kan70T:    5'-CAT CAG AGC AGC CAA TTG TCT GTT GTG CCC AGT
           CGT AGC CGA ATA GCC TCT CCA CCC AAG CGG CCG GAG
           A-3'

FUSION GENE FOR LIGAND BINDING

SEQUENCE LISTING

```
<160> NUMBER OF SEQ ID NOS: 19

<210> SEQ ID NO 1
<211> LENGTH: 70
<212> TYPE: DNA
<213> ORGANISM: Artificial Sequence
<220> FEATURE:
<221> NAME/KEY: stem_loop
<222> LOCATION: (1) ... (54)
<220> FEATURE:
<221> NAME/KEY: stem_loop
<222> LOCATION: (55) ... (70)
<223> OTHER INFORMATION: Description of Artificial Sequence:
      Combined DNA/RNA oligonucleotide for directed alteration of
      kanamycin resistance gene

<400> SEQUENCE: 1
gcuauucggc uaggacuggg cacaauuuut tgtgcccagt cgtagccgaa tagcctctcc        60
uuuuggagag                                                              70

<210> SEQ ID NO 2
<211> LENGTH: 13
<212> TYPE: DNA
<213> ORGANISM: Escherichia coli

<400> SEQUENCE: 2
gtggatatgt cct                                                          13

<210> SEQ ID NO 3
<211> LENGTH: 13
<212> TYPE: DNA
<213> ORGANISM: Escherichia coli

<400> SEQUENCE: 3
gtggatacgt cct                                                          13
```

```
<210> SEQ ID NO 4
<211> LENGTH: 13
<212> TYPE: DNA
<213> ORGANISM: Escherichia coli

<400> SEQUENCE: 4
gtggataggt cct                                                          13

<210> SEQ ID NO 5
<211> LENGTH: 14
<212> TYPE: DNA
<213> ORGANISM: Escherichia coli

<400> SEQUENCE: 5
gtggataatg tcct                                                         14

<210> SEQ ID NO 6
<211> LENGTH: 12
<212> TYPE: DNA
<213> ORGANISM: Escherichia coli

<400> SEQUENCE: 6
gtggatagtc ct                                                           12

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: (1)...(3)
<220> FEATURE:
<221> NAME/KEY: misc_feature
<222> LOCATION: (22)...(24)
<223> OTHER INFORMATION: Description of Artificial Sequence:
      Oligonucleotide with phosphorothioate linkages for directed
      alteration of hygromycin resistance gene

<400> SEQUENCE: 7
agggcgtgga tacgtcctgc gggta                                             25

<210> SEQ ID NO 8
<211> LENGTH: 74
<212> TYPE: DNA
<213> ORGANISM: Artificial Sequence
<220> FEATURE:
<221> NAME/KEY: misc_feature
<222> LOCATION: (1)...(3)
<220> FEATURE:
<221> NAME/KEY: misc_feature
<222> LOCATION: (71)...(73)
<223> OTHER INFORMATION: Description of Artificial Sequence:
      Oligonucleotide with phosphorothioate linkages for directed
      alteration of hygromycin resistance gene

<400> SEQUENCE: 8
ctcgtgcttt cagcttcgat gtaggagggc gtggatacgt cctgcgggta aatagctgcg       60
ccgatggttt ctac                                                         74

<210> SEQ ID NO 9
<211> LENGTH: 74
<212> TYPE: DNA
<213> ORGANISM: Artificial Sequence
<220> FEATURE:
<221> NAME/KEY: misc_feature
<222> LOCATION: (1)...(3)
```

```
<220> FEATURE:
<221> NAME/KEY: misc_feature
<222> LOCATION: (72)...(74)
<223> OTHER INFORMATION: Description of Artificial Sequence:
      Oligonucleotide with phosphorothioate linkages for directed
      alteration of hygromycin resistance gene

<400> SEQUENCE: 9
gtagaaacca tcggcgcagc tatttacccg caggacgtat ccacgccctc ctacatcgaa    60
gctgaaagca cgag                                                      74

<210> SEQ ID NO 10
<211> LENGTH: 70
<212> TYPE: DNA
<213> ORGANISM: Artificial Sequence
<220> FEATURE:
<221> NAME/KEY: stem_loop
<222> LOCATION: (1)...(54)
<220> FEATURE:
<221> NAME/KEY: stem_loop
<222> LOCATION: (55)...(70)
<223> OTHER INFORMATION: Description of Artificial Sequence:
      Combined DNA/RNA oligonucleotide for directed alteration of
      hygromycin resistance gene

<400> SEQUENCE: 10
agggcgugga taggtccugc ggguattttt acccgcagga cgtatccacg ccctcctaca    60
tttttgtagg                                                           70

<210> SEQ ID NO 11
<211> LENGTH: 70
<212> TYPE: DNA
<213> ORGANISM: Artificial Sequence
<220> FEATURE:
<221> NAME/KEY: misc_feature
<222> LOCATION: (1)...(3)
<220> FEATURE:
<221> NAME/KEY: misc_feature
<222> LOCATION: (67)...(69)
<223> OTHER INFORMATION: Description of Artificial Sequence:
      Oligonucleotide with phosphorothioate linkages for directed
      alteration of kanamycin resistance gene

<400> SEQUENCE: 11
catcagagca gccaattgtc tgttgtgccc agtcgtagcc gaatagcctc tccacccaag    60
cggccggaga                                                           70

<210> SEQ ID NO 12
<211> LENGTH: 15
<212> TYPE: DNA
<213> ORGANISM: Escherichia coli

<400> SEQUENCE: 12
ttcggctagg actgg                                                     15

<210> SEQ ID NO 13
<211> LENGTH: 15
<212> TYPE: DNA
<213> ORGANISM: Escherichia coli

<400> SEQUENCE: 13
aagccgatcc tgacc                                                     15

<210> SEQ ID NO 14
<211> LENGTH: 15
<212> TYPE: DNA
```

```
<213> ORGANISM: Escherichia coli

<400> SEQUENCE: 14
ttcggctacg actgg                                                          15

<210> SEQ ID NO 15
<211> LENGTH: 15
<212> TYPE: DNA
<213> ORGANISM: Escherichia coli

<400> SEQUENCE: 15
aagccgatgc tgacc                                                          15

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence:
      FlAsH peptide sequence

<400> SEQUENCE: 16

Arg Val Asp Ala Ala Ala Arg Glu Ala Cys Cys Arg Glu Cys Cys Ala
  1               5                  10                  15

Arg Ala Ile

<210> SEQ ID NO 17
<211> LENGTH: 74
<212> TYPE: DNA
<213> ORGANISM: Artificial Sequence
<220> FEATURE:
<223> OTHER INFORMATION: Description of Artificial Sequence:
      Oligonucleotide for directed alteration of hygromycin
      resistance gene

<400> SEQUENCE: 17
ctcgtgcttt cagcttcgat gtaggagggc gtgggtacgt cctgcgggta aatagctgcg         60
ccgatggttt ctac                                                           74

<210> SEQ ID NO 18
<211> LENGTH: 74
<212> TYPE: DNA
<213> ORGANISM: Artificial Sequence
<220> FEATURE:
<223> OTHER INFORMATION: Description of Artificial Sequence:
      Oligonucleotide for directed alteration of hygromycin
      resistance gene

<400> SEQUENCE: 18
ctcgtgcttt cagcttcgat gtaggagggc gtggatacgt cctgcgggta aacagctgcg         60
ccgatggttt ctac                                                           74

<210> SEQ ID NO 19
<211> LENGTH: 74
<212> TYPE: DNA
<213> ORGANISM: Artificial Sequence
<220> FEATURE:
<223> OTHER INFORMATION: Description of Artificial Sequence:
      Oligonucleotide for directed alteration of hygromycin
      resistance gene
```

```
<400> SEQUENCE: 19
ctcgtgcttt cagcttcgat gtaggagggc gtggatacgt cctgcgggta aatagctgcg      60
ccgacggttt ctac                                                        74
```

COMPOSITIONS AND METHODS FOR ENHANCING OLIGONUCLEOTIDE-MEDIATED GENE ALTERATION

CROSS-REFERENCE TO RELATED APPLICATIONS

This application claims benefit of priority from U.S. Application No. 60/326,041, filed Sep. 27, 2001; U.S. Application No. 60/337,129, filed Dec. 4, 2001 and U.S. Application No. 60/393,330, filed Jul. 1, 2002, the disclosures of which are incorporated herein by reference in their entireties.

FIELD OF THE INVENTION

This invention relates to oligonucleotide-directed repair or alteration of nucleic acid sequence and methods and compositions for enhancing the efficiency of such alteration.

BACKGROUND OF THE INVENTION

A number of different poly- and oligo-nucleotides have been described for use in targeted alteration of nucleic acid sequence including chimeric RNA-DNA oligonucleotides that fold into a double-stranded, double hairpin conformation and single-stranded chemically modified oligonucleotides. These oligonucleotides have been shown to effect targeted alteration of single base pairs as well as frameshift alterations in a variety of host organisms, including bacteria, fungi, plants and animals.

Several cellular pathways and gene groups are believed to be involved in mediating in vivo repair of DNA lesions resulting from radiation or chemical mutagenesis, including the RAD52 epistasis group of proteins, the mismatch repair group of proteins and the nucleotide excision repair group of proteins. The role of these proteins in homologous recombination and maintaining genome integrity has been extensively studied and is reviewed, for example, in Heyer, *Experientia* 50(3), 223–233 (1994); Thacker, *Trends in Genetics* 15(5), 166–168 (1999); Paques & Haber, *Microbiol. and Molec. Biol. Rev.* 63(2), 349–404 (1999); and Thompson & Schild, *Mutation Res.* 477, 131–153 (2001). The specific function of these proteins in oligonucleotide-directed nucleic acid sequence alteration is not well understood.

The utility of oligonucleotide-directed nucleic acid sequence alteration as a means, for example, to generate agricultural products with enhanced traits or to generate animal models or animals with desired traits is affected by its frequency. The utility of oligonucleotide-directed nucleic acid sequence alteration as a therapeutic method would also be enhanced by increasing its efficiency. A need exists for methods to enhance the efficiency of oligonucleotide-directed nucleic acid sequence alteration.

SUMMARY OF THE INVENTION

As used herein, "target nucleic acid sequence" or "target sequence" are used interchangeably to refer to the starting nucleic acid sequence that the "oligonucleotide having a nucleic acid sequence alteration" (i.e., "sequence altering oligonucleotide") is directed, such that the "sequence altering oligonucleotide" is complementary to the "target sequence" except for specific sites of base pair mismatch that, according to the methods of the invention, result in the intended target sequence alteration.

As used herein, the term "homolog" refers to a nucleic acid sequence or amino acid sequence of a particular gene that is derived from different species. A "homologous nucleic acid sequence" or "homologous amino acid sequence," or variations thereof, refer to sequences characterized by a homology at the nucleotide level or amino acid level as discussed above. Nucleic acids are homologous when they are derived, naturally or artificially, from a common ancestor sequence. If the homology between two nucleic acids is not expressly described, homology can be inferred by a nucleic acid comparison between two or more sequences. If the sequences demonstrate some degree of sequence similarity it is concluded that they share a common ancestor. The degree of similarity will vary and important factors include for example, the degree of overall similarity, the degree of similarity within specific regions of the coding sequence, the similarity of noncoding sequence, and the activity of the polypeptide. For purposes of the present invention, genes are homologous if the sequences are sufficiently similar to allow recombination.

As used herein, "paralog" refers to a situation where the homology between two or more sequences is the result of gene duplication so that both copies have descended side by side during the history of an organism, (for example, alpha and beta hemoglobin).

As used herein, "ortholog" refers to a situation where the homology between two or more sequences is the result of speciation so that the history of the gene reflects the history of the species (for example alpha hemoglobin in man and mouse).

As used herein, the phrase "altered levels and/or activity" refers to a comparison of the normal or wild type DNA repair capacity of a cell or cell extract with a cell or cell extract comprising altered expression or activity of RAD10, RAD51, RAD52, RAD54, RAD55, MRE11, PMS1, XRS2 or a combination thereof.

The present invention concerns methods and compositions for enhancing oligonucleotide-directed nucleic acid sequence alteration in vivo, ex vivo, and in vitro. Without being limited by theory, it is believed that certain DNA repair proteins are involved in oligonucleotide-directed nucleic acid sequence alteration. However, because these proteins function through multiple complex interactions and because oligonucleotide-directed nucleic acid sequence alteration relies on the activity of molecules that have alternative chemistries as compared to products resulting from radiation or chemical mutagens, whether or how any of these proteins would be involved was unknown and unpredictable prior to this invention.

The invention involves methods of targeted nucleic acid sequence alteration using cells or extracts with altered levels or activity of at least one protein from the RAD52 epistasis group, the mismatch repair group or the nucleotide excision repair group. Generally, in instances where genes are identified herein by gene name, e.g., RAD52, the allele represented is one which is recognized as having normal, wild-type activity identified using the yeast (*Saccharomyces cerevisiae*) nomenclature. Where the genes have a mutation resulting in reduced or eliminated activity, the gene will be so identified in writing or will be italicized and in lowercase, e.g. rad52. Where a mutation is a deletion of the gene it may also be represented with a Greek letter delta, i.e. Δ. Although these designations use the yeast nomenclature, it is to be understood that homologous proteins, e.g. homologs, orthologs and paralogs, from other organisms, including bacteria, plants, animals and other fungi may be used in the methods of the instant invention. Members of these groups include: RAD50, RAD51, RAD52, RAD54, RAD55, RAD57, RAD59, MRE11 and XRS2 in the RAD52 epistasis group; MSH2, MSH3, MSH6 and PMS1 in the mismatch repair group; and RAD1, RAD2, RAD10, RAD23 and EXO1 in the nucleotide excision repair group.

In another aspect, the invention relates to kits comprising a cell or cell-free extract with increased levels of at least one of the normal allelic RAD10, RAD51, RAD52, RAD54, RAD55, MRE1, PMS1 or XRS2 proteins or with increased activity of one of these proteins. In further embodiments, the kits comprise a cell or cell-free extract with increased levels or activity of at least one of the RAD10, RAD51, RAD52, RAD54, RAD55, MRE11, PMS1 or XRS2 proteins and decreased levels or activity of at least one protein selected from the group consisting of RAD1, RAD51, RAD52, RAD57 or PMS1. In other embodiments, the kits further comprise at least one oligonucleotide capable of directing nucleic acid sequence alteration. In some embodiments, the kits may include multiple oligonucleotides.

In different embodiments, the invention relates to kits comprising at least one oligonucleotide capable of directing nucleic acid sequence alteration and at least one purified protein selected from the group consisting of the RAD10, RAD51, RAD52, RAD54, RAD55, MRE11, PMS1 or XRS2 proteins. Other kits may comprise multiple oligonucleotides.

In still other embodiments, the present invention relates to processes to alter plant genomes by administering to a plant cell or tissue at least one oligonucleotide having a desired nucleic acid sequence alteration sequence, wherein the plant cell or tissue has altered levels and/or activity of a protein encoded by a plant which is homologous to a RAD10, RAD51, RAD52, RAD54, RAD55, MRE11, PMS1 or XRS2 gene. The plant cell can be used to generate plants which are a further embodiment of the invention. The invention further relates to methods for genetically altering plants to enhance or generate desirable traits, for example, herbicide or pest resistance.

In a further embodiment, the present invention relates to a process to genetically alter animals, particularly livestock, to enhance expression of desirable traits, comprising administering to a target cell at least one oligonucleotide having a nucleic acid sequence alteration sequence, wherein the cell has altered levels and/or activity of a protein encoded by a gene homologous to the RAD10, RAD51, RAD52, RAD54, RAD55, MRE11, PMS1 or XRS2 gene from yeast and the animals produced thereby.

In a further embodiment, the present invention relates to an assay to identify activators of RAD10, RAD51, RAD52, RAD54, RAD55, MRE11, PMS1 and/or XRS2 protein activity and/or one or more activators of RAD10, RAD51, RAD52, RAD54, RAD55, MRE11, PMS1 or XRS2 gene expression comprising contacting a sample with an oligonucleotide in a system known to provide for nucleic acid sequence alteration and measuring whether the amount of nucleic acid sequence alteration is less, more, or the same as in the absence of sample. In another embodiment this assay may be used to identify mutations in the genes encoding the RAD10, RAD51, RAD52, RAD54, RAD55, MRE11, PMS1, or XRS2 protein that increase or decrease their activity. In some embodiments of the invention, the RAD10, RAD51, RAD52, RAD54, RAD55, MRE11, PMS1 or XRS2 gene product is increased in amount or activity. In other embodiments of the invention, the RAD10, RAD51, RAD52, RAD54, MRE11, PMS1 or XRS2 gene product is increased in amount or activity by complementation or supplementation and the complemented or supplemented cell contains a knock-out mutation of the RAD52 gene.

BRIEF DESCRIPTION OF THE DRAWINGS

In FIG. 3, the sequence of HygE3T/25 corresponds to SEQ ID NO: 7, the sequence of HygE3T/74 corresponds to SEQ ID NO: 8, the sequence of HygE3T/74 a corresponds to SEQ ID NO: 9, the sequence of HygGG/ Rev corresponds to SEQ ID NO: 10 and the sequence of Kan70T corresponds to SEQ ID NO: 11.

In FIG. 9, the sequence of the Neo/kan target mutant corresponds to SEQ ID NO: 12 and SEQ ID NO: 13, the converted sequence corresponds to SEQ ID NO: 14 and SEQ ID NO: 15 and the FlAsH peptide sequence corresponds to SEQ ID NO: 16.

DETAILED DESCRIPTION OF THE INVENTION

Figure 1:
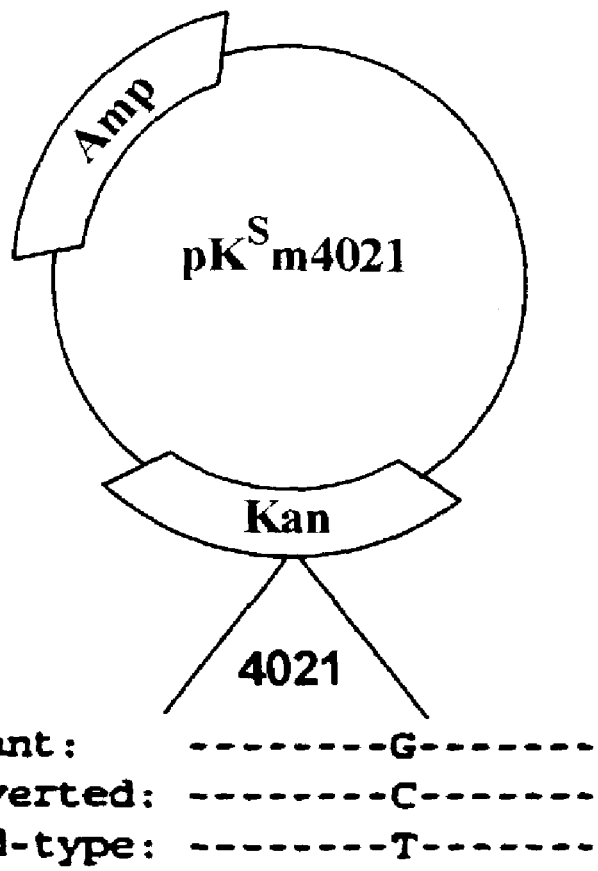
FIG. 1. Genetic readout system for alteration of a point mutation in plasmid pK$^s$m4021. A mutant kanamycin gene harbored in plasmid pK$^s$m4021 is the target for alteration by oligonucleotides. The mutant G is converted to a C by the action of the oligonucleotide. Corrected plasmids confer resistance to kanamycin in E. coli (DH10B) after electroporation leading to the genetic readout and colony counts. The sequence of chimeric, RNA-DNA double-hairpin oligonucleotide KanGG is shown (SEQ ID NO: 1).
Figure 1:
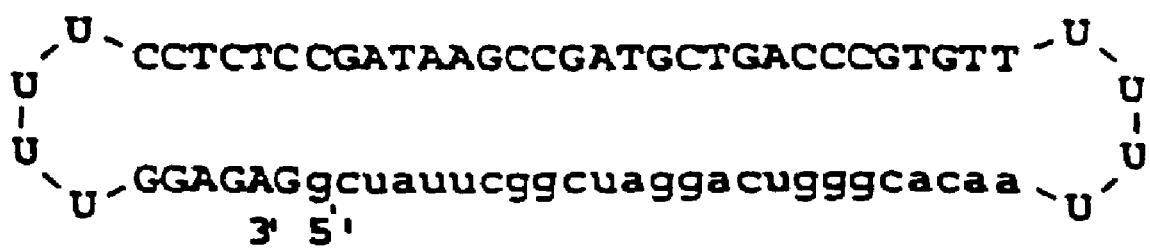

The present invention involves methods of nucleic acid sequence alteration comprising administering to a cell or tissue from a bacterium, a fungus, a plant, or an animal an oligonucleotide having a nucleic acid sequence alteration sequence as compared to the targeted sequence wherein the target cell or tissue has altered levels or activity of at least one protein from the RAD52 epistasis group, the mismatch repair group or the nucleotide excision repair group. Altering the levels or activity of these proteins can be decreasing or increasing the levels or activity of a protein or a combination of proteins. Decreasing the levels or activity can be achieved by any means known to one of skill in the art, including, for example, using inhibitors of the activity of one of the proteins, suppressors of expression of one of the genes, or a mutation in one of the genes that decreases the expression or the activity of the protein. Similarly, increasing the levels or activity can be achieved by any means known to one of skill in the art, including, for example, using activators of the activity of one of the proteins, activators of expression of one of the genes, a mutation in one or more of the gene products that increases the expression or the activity of the protein, or addition of extra copies of one of the proteins or genes by, for example, complementation or supplementation. The addition of extra copies of one of the proteins or genes can be achieved, for example, by directing expression of the gene using a constitutive or inducible promoter and/or an enhancer or by adding extra copies of an expressed or expressible nucleic acid molecule encoding a protein or gene.

The methods of the present invention can be used with any oligonucleotide having nucleic acid sequence alteration activity including, for example, chimeric, RNA-DNA double hairpin oligonucleotides and modified, single-stranded oligonucleotides. Such oligonucleotides are described, for example, in U.S. Pat. No. 5,945,339; U.S. Pat. No. 5,795,972; U.S. Pat. No. 5,871,984 and International Patent Application PCT/US01/09761 which are hereby incorporated by reference in their entireties. See also, for example, International Patent Application PCT/US01/23770, "Compositions and Methods for Enhancing Oligonucleotide-Mediated Gene Alteration," filed Jul. 27, 2001, which is incorporated by reference herein in its entirety. For examples of single-stranded chemically modified oligonucleotides useful in the methods of the invention, see U.S. Patent Application No. 60/244,989, "Targeted Chromosomal Genomic Alterations with Modified Single Stranded Oligonucleotides," filed Oct. 30, 2000, International Patent Application PCT/US01/09761 "Targeted Chromosomal Genomic Alterations with Modified Single Stranded Oligonucleotides," filed Mar. 27, 2001, and International Patent Application PCT/US01/17672 "Targeted Chromosomal Genomic Alterations in Plants Using Modified Single-Stranded Oligonucleotides," filed Jun. 1, 2001, which are all incorporated by reference herein in their entireties.

Oligonucleotides designed to direct nucleic acid sequence alteration comprise a portion that is generally identical in sequence to a portion of a target DNA sequence or a portion of the complement of a target DNA sequence except for any specific difference or differences designed to direct nucleic acid sequence alteration. Thus, the oligonucleotides used in the methods of the invention have at least one base pair different from the sequence of the target DNA, or have at least one base pair different from the complement of the sequence of the target DNA. The methods of the invention can be used to enhance the alteration directed by an oligonucleotide directing any kind of alteration, including, for example, deletion, insertion or replacement of 1, 2 or 3 nucleotides in the target sequence. These altered nucleotides may be contiguous or non-contiguous to each other. Further, nucleic acid sequence alteration by oligonucleotides targeting 1, 2, or 3 multiple sequence alterations is also enhanced using the methods of the instant invention. Each of such multiple alterations can include, for example, deletion, insertion or replacement of 1, 2 or 3 nucleotides in the target sequence. These altered nucleotides may be contiguous or non-contiguous to each other. Where nucleic acid sequence alteration of multiple sequence targets is enhanced, the multiple alterations can be directed by a single oligonucleotide or by 1, 2 or 3 separate oligonucleotides. In some embodiments, the multiple alterations are directed by a single oligonucleotide. In certain embodiments, the multiple alterations are within 1 to 10 nucleotides of each other.

The oligonucleotides can be introduced into cells or tissues by any technique known to one of skill in the art. Such techniques include, for example, electroporation, liposome transfer, naked nucleic acid insertion, particle bombardment and calcium phosphate precipitation. In one embodiment the transfection is performed with a liposomal transfer compound, for example, DOTAP (N-1-(2,3-Dioleoyloxy)propyl-N,N,N-trimethylammonium methylsulfate, Boehringer-Mannheim) or an equivalent, such as LIPOFECTIN®. Other liposomal transfer compounds include, for example, Lipofectamine™ and Superfect™. In another embodiment, the transfection technique uses cationic lipids. Other methods include the use of macromolecular carriers, including an aqueous-cored lipid vesicle or liposome wherein the oligonucleotide is trapped in the aqueous core. Such vesicles are made by taking a solvent-free lipid film and adding an aqueous solution of the oligonucleotide, followed by vortexing, and extrusion or passage through a microfiltration membrane. In one embodiment the lipid constituents are a mixture of dioleoyl phosphatidylcholine/ dioleoyl phosphatidylserine/galactocerebroside at a ratio of 1:1:0.16. Other carriers include polycations, such as polyethylenimine, having a molecular weight of between 500 daltons and 1.3 Md, with 25 kd being a suitable species and lipid nanospheres, wherein the oligonucleotide is provided in the form of a lipophilic salt.

The methods of the invention can be used with a wide range of concentration of oligonucleotides. For example, good results can be achieved with 10 nM/$10^5$ cells. A ratio of about 500 ng of oligonucleotide in 3 μg of DOTAP per $10^5$ cells can be used. The transfected cells may be cultured in different media, including, for example, in serum-free media, media supplemented with human serum albumin or human serum.

The methods of the instant invention can be used to enhance the efficiency of nucleic acid sequence alteration directed by an oligonucleotide that targets either strand of a double-stranded target nucleic acid. The methods of the invention can be used to enhance the efficiency of an oligonucleotide targeting a gene, including any part of a gene, for example, an exon, an intron, a promoter, an enhancer or a 3'- or 5'-untranslated region. Further, the methods of the invention can be used to enhance the efficiency of an oligonucleotide targeting intragenic sequences. In some embodiments, these methods are used to enhance the efficiency of an oligonucleotide targeting actively transcribed sequences. In some embodiments, these methods are used to enhance the efficiency of an oligonucleotide targeting the non-transcribed strand of the target sequence.

The methods of the invention involve the alteration of the expression or the activity of at least one protein selected from the group consisting of the RAD52 epistasis group proteins RAD51, RAD52, RAD54, RAD55, MRE11 and XRS2, the mismatch repair group protein PMS1, and the nucleotide excision repair group protein RAD10. The symbols for these proteins are taken from the yeast (*Saccharomyces cerevisiae*) designations, but it is understood that homologous proteins, including homologs, orthologs and paralogs from other organisms, including bacteria, plants, animals and other fungi can be used in the methods of the instant invention. Example sequences from bacteria and fungi include MUTL from *Bacillus subtilis* (GenBank™ Acc. No. P49850), RHP57 from *Schizosaccharomyces pombe* (GenBank™ Acc. No. T43507), UVSC from *Emericella nidulans* (GenBank™ Acc. No. CAB02454), PMS1 from *S. pombe* (GenBank™ Acc. No. P54280), MUS38 from *Neurospora crassa* (GenBank™ Acc. No. BAA28847), RAD52 from *Kluyveromyces lactis* (GenBank™ Acc. No. P41768), RAD52 from *S. pombe* (GenBank™ Acc. No. P36592), MUS11 from *N. crassa* (GenBank™ Acc. No. BAB13343), RAD 51 from *S. pombe* (GenBank™ Acc. No. P36601), RAD51 from *Ustilago maydis* (GenBank™ Acc. No. Q99133), RAD51 from *E. nidulans* (GenBank™ Acc. No. P78579) and RAD51 from *Penicillium paxilli* (GenBank™ Acc. No. BAA92869). Example sequences from plants include DMC1 from *Glycine max* (GenBank™ Acc. No. Q96449), MUA2.3 from *Arabidopsis thaliana* (GenBank™ Acc. No. BAB08781), UVH1 from *A. thaliana* (GenBank™ Acc. No. AAF01274), RAD51 from *A. thaliana* (GenBank™ Acc. No. P94102) and RAD51 from *Lycopersicon esculentum* (GenBank™ Acc. No. Q40134). Example sequences from animals, including humans, include human XRCC3 (GenBank™ Acc. No. AAC04805), mouse RAD51 (GenBank™ Acc. No. NP_033040), spindle B from *Drosophila melanogaster* (GenBank™ Acc. No. AAC42663), human PMS2 (GenBank™ Acc. No. P54278), mouse PMS2 (GenBank™ Acc. No. P54279), human PMS1 (GenBank™ Acc. No. P54277), human MLH1 (GenBank™ Acc. No. P40692), ERCC4 from *Cricetulus griseus* (GenBank™ Acc. No. BAA89229), human ERCC4 (GenBank™ Acc. No. NP_005227), mouse XPF (GenBank™ Acc. No. NP_056584), MEI-9 from *D. melanogaster* (GenBank™ Acc. No. AAF45938), human RAD52 (GenBank™ Acc. No. AAF05533), mouse RAD52 (GenBank™ Acc. No. P43352), chicken RAD52 (GenBank™ Acc. No. P39022), RAD51 from *C. griseus* (GenBank™ Acc. No. P70099), human RAD51 (GenBank™ Acc. No. Q06609), chicken RAD51 (GenBank™ Acc. No. P37383), mouse RAD51 (GenBank™ Acc. No. 035719), rabbit RAD51 (GenBank™ Acc. No. 077507), RAD51 from *Xenopus laevis* (GenBank™ Acc. No. Q91918), RAD51 from *Bombyx mori* (GenBank™ Acc. No. 001679) and RAD51 from *D. melanogaster* (GenBank™ Acc. No. Q27297).

The alteration of the expression or the activity of the at least one protein can be either increasing or reducing the expression or activity of the protein. Where the alteration is increasing the expression or the activity, the increase in expression or activity can be about one, two, three, four, five, six, seven, eight, nine, ten, twelve, fifteen, twenty, thirty, and fifty or more fold. Similarly, where the alteration is reducing the expression or the activity, the decrease in expression or activity can be about one, two, three, four, five, six, seven, eight, nine, ten, twelve, fifteen, twenty, thirty, and fifty or more fold. Reducing the expression or the activity of the protein can also be achieved by completely eliminating the expression or the activity of the target protein. In certain embodiments of the invention, the expression or activity of at least one protein is increased and the expression or activity of at least one other protein is decreased.

Any method for altering the expression or the activity of the above-described proteins known to one of skill in the art can be employed in the methods of the instant invention. Methods for increasing, reducing or eliminating the expression or the activity of the above-described proteins include generating mutations in the targeted gene from the RAD52 epistasis group gene, mismatch repair group gene or nucleotide excision repair group gene. Such mutations may be engineered in the host organism using any method known to those of skill in the art, including, for example, using a chimeric, RNA-DNA double hairpin or modified, single-stranded oligonucleotide; isolating a spontaneous mutation; and selecting/screening from a mutagenized population. These methods can be combined, for example, to identify a useful mutation in one organism or cell and then engineering the specific mutation in a homologous gene of a second organism or cell. Any type of mutation in the RAD52 epistasis group gene, mismatch repair group gene or nucleotide excision repair group gene that results in the desired effect can be used for the methods of the instant invention including, for example, missense, deletion, insertion, transposon, and retroposon.

Well known methods for reducing or eliminating the expression or the activity of the above-described proteins also include engineering extragenic elements, including, for example, antisense methods, ribozyme methods, cosuppression, gene silencing methods, RNA interference ("RNAi") methods, and using triplex-forming oligonucleotides.

Antisense methods involve the introduction or expression of a nucleic acid molecule that has sufficient complementarity to a transcript encoding the protein. An antisense nucleic acid molecule does not have to be 100% complementary to the target in order to have sufficient complementary to exert an antisense effect. Generally, an antisense nucleic acid molecule is at least 90% complementary in sequence to the target transcript, for example, at least 95%, at least 98%, at least 99% or 100% complementary. In order to cause an antisense-effect, antisense oligonucleotides are generally 10–40 nucleotides long, typically 15–30 nucleotides in length. For in vivo expressed antisense, oligonucleotides preferably have a length of at least 100 nucleotides and more preferably a length of at least 500 nucleotides. It is also preferred that in vivo expressed antisense nucleic acid molecules are no more than about 5000 nucleotides in length, more preferably no more than about 2500 nucleotides. Such antisense polynucleotides can be produced in vivo by transcription or they can be introduced as oligo- or polynucleotides. For antisense oligonucleotides, it is preferred that the oligonucleotides comprise at least one PNA, LNA, or 2'-O-methyl RNA residue or at least one phosphorothioate backbone linkage to reduce their degradation.

The antisense nucleic acid molecules useful as suppressors of gene expression in the methods of the invention are typically administered to a subject or generated in situ such that they hybridize with or bind to cellular mRNA encoding a polypeptide to thereby inhibit expression of the polypeptide, for example, by inhibiting transcription and/or translation. The hybridization is generally by conventional nucleotide complementarity to form a stable duplex. Examples of routes of administration of an antisense nucleic acid molecule include direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, for example, by linking the antisense nucleic acid molecule to a peptide or an antibody which binds to a cell surface receptor or antigen. The antisense nucleic acid molecule can also be delivered to cells using one of the methods for delivering the nucleic acid sequence altering oligonucleotides as described herein. To achieve sufficient intracellular concentrations of the antisense molecules using an in vivo expressed antisense nucleic acid molecule, vector constructs in which the antisense nucleic acid molecule is placed under the control of a strong promoter are preferred.

Cosuppression methods relate to RNA molecules which reduce the expression in a host cell of the nucleic acid molecule encoding the target protein due to a cosuppression-effect. The principle of the cosuppression as well as the production of corresponding DNA sequences is well known in the art and is described, for example, in WO 90/12084. Such DNA molecules preferably encode an RNA having a high degree of homology to the target transcript. While cosuppressing RNA molecules are the same sense as an RNA molecule encoding the protein, it is not necessary for cosuppression that the RNA molecule actually encodes a polypeptide. For example, an RNA with nonsense mutations but substantial sequence similarity to the target nucleic acid molecule can effectively cosuppress.

RNAi refers to the introduction of homologous double-stranded RNA (dsRNA) to specifically target a gene transcript, resulting in null or hypomorphic levels of the resulting protein. RNAi methods are highly sequence-specific and very sensitive with only a few dsRNA molecules required per cell for effective interference. RNAi methods are known in the art and are described, for example, in WO 99/32619, WO 00/63397 and WO 01/68836.

Yet another method for reducing the expression or the activity of the target protein involves RNA molecules with a ribozyme activity which specifically cleave transcripts encoding one of the above-described DNA repair proteins. Ribozymes are catalytically active RNA molecules capable of cleaving RNA molecules and specific target sequences. There are various classes of ribozymes, but the group I intron type and the "hammerhead" motif type are preferred for the methods of the invention. The specific recognition of the target RNA molecule may be modified by altering the sequences flanking this motif. These recognition sequences pair with sequences in the target molecule and determine the position of cleavage in the target molecule. The sequence requirements for efficient cleavage are extremely low and a specific ribozyme can be designed for almost any desired target.

Alternatively, gene expression can be inhibited by targeting nucleotide sequences complementary to the regulatory region of the target gene (e.g., a promoter and/or enhancer) to form triple helical structures that prevent transcription of the gene in target cells. For example, using a nucleic acid molecule which binds to DNA duplexes through specific interactions with the double helix. Such nucleic acid molecules are generally 12–40 nucleotides in length, typically 25–35 nucleotides in length. See, generally, Helene, C. (1991) *Anticancer Drug Des*. 6(6):569–84; Helene, C. et al. (1992) *Ann. N.Y. Acad. Sci*. 660:27–36; and Maher, L. J. (1992) *Bioassays* 14(12):807–15.

Methods for increasing the expression or the activity of proteins are well known to one of ordinary skill in the art and include, for example, using activators of the activity of one of the proteins, activators of expression of one of the genes, a mutation in one of the genes that increases the expression or the activity of the protein, or addition of extra copies of one of the proteins or genes. The addition of extra copies of one of the proteins or genes can be achieved, for example, by directing expression of the gene using a constitutive or inducible promoter and/or an enhancer or by adding extra copies of a nucleic acid molecule encoding a protein or gene.

Surprisingly, different alterations in the levels or activity of the proteins of the RAD52 epistasis group, mismatch repair group or nucleotide excision repair group influence the efficiency of nucleic acid sequence alteration differently. For example, in compositions and methods with reduced or eliminated expression or activity of the proteins of the RAD52 epistasis group, mismatch repair group or nucleotide excision repair group, it is preferred that the protein is selected from RAD1, RAD51, RAD52, RAD57 or PMS1. See, for example, International Patent Application PCT/US01/23770, filed Jul. 27, 2001, which is incorporated herein by reference in its entirety. This application demonstrates that nucleic acid sequence alteration activity is enhanced in compositions and methods with increased expression or activity of proteins of the RAD52 epistasis group, mismatch repair group or nucleotide excision repair group, including a protein selected from RAD10, RAD51, RAD52, RAD54, RAD55, MRE11, PMS1 or XRS2. The instant application further demonstrates that it is preferred that the levels of RAD51 are increased and the levels of RAD52 are decreased.

The examples in this application further demonstrate methods and assay systems to identify and optimize which background mutations and/or activity alterations to use to achieve enhanced nucleic acid sequence alteration efficiency for an oligonucleotide that introduces a desired sequence alteration, including, for example, an insertion, deletion, or replacement alteration as described herein as well as oligonucleotides that introduce multiple alterations. One of skill in the art could readily modify one of these systems to assay alteration of any target to optimize the strain background for introduction of desired nucleic acid sequence alterations using the teachings of this application. Generally, a protein selected from the group of RAD10, RAD51, RAD52, RAD54, RAD55, MRE11, PMS1 or XRS2 is increased to effect the alteration of a targeted gene sequence by any of the oligonucleotides of the invention. In one embodiment, the product of the RAD52 chromosomal gene is completely defective due to a knock-out mutation and the cell is complemented or supplemented with any one of the protein products of the RAD51, RAD52, RAD55, MRE11, PMS1 or XRS2 genes provided in trans on a plasmid in which the protein product is constitutively expressed. In another embodiment, the product of the RAD52 chromosomal gene is completely defective due to a knock-out mutation and the cell is complemented or supplemented with the protein product of the RAD51 gene provided in trans on a plasmid in which the RAD51 protein product is constitutively expressed.

The methods of the instant invention also can be used to enhance the efficiency of nucleic acid sequence alteration in vitro using cell-free extracts. The cell-free extract can be derived from cells or tissue from any organism including bacteria, fungi, plants, and animals, including humans or other mammals. Cells or cell-free extracts for use in the methods and compositions of the invention include, for example, cultured cells of human liver, lung, colon, cervix, kidney, epithelium. Additional cells or cell-free extracts for use in the methods and compositions of the invention include, for example, COS-1 and COS-7 cells (African green monkey), CHO-K1 cells (Chinese hamster ovary), H1299 cells (human epithelial carcinoma, non-small cell lung cancer), C1271 (immortal murine mammary epithelial cells), MEF (mouse embryonic fibroblasts), HEC-1-A (human uterine carcinoma), HCT15 (human colon cancer), HCT116 (human colon carcinoma), LoVo (human colon adenocarcinoma), and HeLa (human cervical carcinoma) cancer cells as well as PG12 cells (rat pheochromocytoma) and ES cells (human embryonic stem cells). The extract can be derived from any source, including, for example cultured cells, primary isolated cells, or tissue. The extract can be derived from a cell or tissue, wherein the levels or activity in the extract of at least one protein selected from the group consisting of RAD10, RAD51, RAD52, RAD54, RAD55, MRE11, PMS1 or XRS2 is altered.

The methods of the instant invention also can be used to enhance the efficiency of nucleic acid sequence alteration in a cell ex vivo. The cell can be derived from cells or tissue from any organism including bacteria, fungi, plants, and animals, including humans or other mammals. Cells or cell-free extracts for use in the methods and compositions of the invention include, for example, lymphocytes and stem cells.

As with the in vivo methods of the invention, the alteration in cell-free extracts of the expression or the activity of the at least one protein can be either increasing or reducing the expression or activity of the protein. Where the alteration is increasing the expression or the activity, the increase in expression or activity can be about one, two, three, four, five, six, seven, eight, nine, ten, twelve, fifteen, twenty, thirty, and fifty or more fold. Similarly, where the alteration is reducing the expression or the activity, the decrease in expression or activity can be about one, two, three, four, five, six, seven, eight, nine, ten, twelve, fifteen, twenty, thirty, and fifty or more fold. Reducing the expression or the activity of the protein can also be achieved by completely eliminating the expression or the activity of the target protein.

Cell-free extract with altered levels and/or activity of a protein or proteins can be used in the methods of the invention. For this purpose, any method known to one of skill in the art, including the methods described herein, can be employed to alter (including increasing, decreasing or eliminating) the expression or the activity of protein or proteins in a cell before obtaining cell-free extract therefrom. For example, it is possible to reduce the levels or the activity of a protein by depleting the protein from the cell-free extract by any means known to one of skill in the art, including, for example, addition of extra copies of interacting proteins, immunoprecipitation, immunosequestration, or specific degradation of the target protein. As an additional example, it is possible to increase the levels or activity by supplementing the extract with at least one purified protein in the RAD52 epistasis group, the mismatch repair group or the nucleotide excision repair group.

Methods of enhancing nucleic acid sequence alteration using cell-free extracts with altered levels or activity of at least one protein selected from the group consisting of RAD10, RAD51, RAD52, RAD54, RAD55, MRE11, PMS1 or XRS2 are particularly useful for oligonucleotide-directed alteration of isolated episomal targets, including, for example, plasmids, cosmids, artificial chromosomes, YACs, BACs, PLACs, and BiBACS. However, the in vitro methods may be used with any target nucleic acid molecule. Similarly, methods of the invention for enhancing nucleic acid sequence alteration alteration in vivo can be used with any target nucleic acid molecule in cells, including, for example, genomic or chromosomal targets, organellar genomic targets, and episomal targets.

The present invention relates to a process to genetically alter animals, including livestock, to enhance expression of desirable traits, comprising administering to a target cell at least one oligonucleotide having a nucleic acid sequence alteration sequence, wherein the cell has altered levels and/or activity of at least one protein encoded by a gene that is a homolog, ortholog or paralog of a yeast RAD10, RAD51, RAD52, RAD54, RAD55, MRE11, PMS1 or XRS2 and the animals produced thereby. Alternatively, the process may comprise administering to a target cell at least one oligonucleotide having a nucleic acid sequence alteration sequence and at least one purified protein in the RAD52 epistasis group, the mismatch repair group or the nucleotide excision repair group. In the preferred embodiment, two distinct proteins are manipulated by knocking out one chromosomal gene and complementing or supplementing a second gene product to produce increased or altered levels of the second protein. In one embodiment, the chromosomal RAD52 gene is knocked-out and the cell is complemented or supplemented with the RAD51 gene product expressed in trans under control of a constitutive promoter. The methods of the invention can be used to genetically alter cells from any animal, including, for example, horses, cattle, sheep, pigs, goats, bison; fowl such as chickens, geese, ducks, turkeys, pheasant, ostrich and pigeon; fish such as salmon, tilapia, catfish, trout and bass; model experimental animals such as mice, rats and rabbits; and pets such as dogs and cats.

The present invention encompasses methods for introducing targeted nucleic acid sequence alterations in plants using an effective amount of at least one oligonucleotide containing a nucleic acid sequence alteration sequence in a plant strain having altered levels and/or activity of at least one protein encoded by a plant homolog of a RAD10, RAD51, RAD52, RAD54, RAD55, MRE11, PMS1 or XRS2 gene or activators of a RAD10, RAD51, RAD52, RAD54, RAD55, MRE11, PMS1 or XRS2 gene. Alternatively, the process may comprise administering to a target plant cell at least one oligonucleotide having a nucleic acid sequence alteration sequence and at least one purified protein in the RAD52 epistasis group, the mismatch repair group or the nucleotide excision repair group. Preferred target plants include, for example, experimental model plants such as *Chlamydomonas reinhardtii, Physcomitrella patens*, and *Arabidopsis thaliana* in addition to crop plants such as cauliflower (*Brassica oleracea*), artichoke (*Cynara scolymus*), fruits such as apples (*Malus*, e.g. *domesticus*), mangoes (*Mangifera*, e.g. *indica*), banana (*Musa*, e.g. *acuminata*), berries (such as currant, *Ribes*, e.g. *rubrum*), kiwifruit (*Actinidia*, e.g. *chinensis*), grapes (*Vitis*, e.g. *vinifera*), bell peppers (*Capsicum*, e.g. *annuum*), cherries (such as the sweet cherry, *Prunus*, e.g. *avium*), cucumber (*Cucumis*, e.g. *sativus*), melons (*Cucumis*, e.g. *melo*), nuts (such as walnut, *Juglans*, e.g. *regia*; peanut, *Arachis hypogeae*), orange (*Citrus*, e.g. *maxima*), peach (*Prunus*, e.g. *persica*), pear (*Pyra*, e.g. *communis*), plum (*Prunus*, e.g. *domestica*), strawberry (*Fragaria*, e.g. *moschata* or *vesca*), tomato (*Lycopersicon*, e.g. *esculentum*); leaves and forage, such as alfalfa (*Medicago*, e.g. *sativa* or *truncatula*), cabbage (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*); seeds, including oilseeds, such as beans (*Phaseolus*, e.g. *vulgaris*), pea (*Pisum*, e.g. *sativum*), soybean (*Glycine*, e.g. *max*), cowpea (*Vigna unguiculata*), mothbean (*Vigna aconitifolia*), wheat (*Triticum*, e.g. *aestivum*), sorghum (*Sorghum* e.g. *bicolor*), barley (*Hordeum*, e.g. *vulgare*), corn (*Zea*, e.g. *mays*), rice (*Oryza*, e.g. *sativa*), rapeseed (*Brassica napus*), millet (*Panicum* sp.), sunflower (*Helianthus annuus*), oats (*Avena sativa*), chickpea (*Cicer*, e.g. *arietinum*); tubers, such as kohlrabi (*Brassica*, e.g. *oleraceae*), potato (*Solanum*, e.g. *tuberosum*) and the like; fiber and wood plants, such as flax (*Linum* e.g. *usitatissimum*), cotton (*Gossypium* e.g. *hirsutum*), pine (*Pinus* sp.), oak (*Quercus* sp.), eucalyptus (Eucalyptus sp.), and the like and ornamental plants such as turfgrass (*Lolium*, e.g. *rigidum*), petunia (*Petunia*, e.g. *x hybrida*), hyacinth (*Hyacinthus orientalis*), carnation (*Dianthus* e.g. *caryophyllus*), delphinium (*Delphinium*, e.g. *ajacis*), Job's tears (*Coix lacryma-jobi*), snapdragon (*Antirrhinum majus*), poppy (*Papaver*, e.g. *nudicaule*), lilac (*Syringa*, e.g. *vulgaris*), hydrangea (*Hydrangea* e.g. *macrophylla*), roses (including Gallicas, Albas, Damasks, Damask Perpetuals, Centifolias, Chinas, Teas and Hybrid Teas) and ornamental goldenrods (e.g. *Solidago* spp.). Generally, isolated plant cells or protoplasts are treated according to the methods of the invention and then used to regenerate whole plants according to methods well known in the art.

Relatively few specific plant mutations that produce desirable phenotypes have been described for plant species or cultivars. However, the methods of the instant invention may be used to identify a desirable mutation in one species, for example an experimental model plant, and the desirable mutation can then be introduced in the homologous genes of other species using the methods of the invention. Further, the methods of the invention can be used to produce "knock out" mutations by modification of specific amino acid codons to produce stop codons (e.g., a CAA codon specifying glutamine can be modified at a specific site to TAA; a AAG codon specifying lysine can be modified to TAG at a specific site; and a CGA codon for arginine can be modified to a TGA codon at a specific site). Such base pair changes will terminate the reading frame and produce a truncated protein, shortened at the site of the stop codon, which truncated protein is generally defective. Alternatively, frameshift additions or deletions can be directed into the genome at a specific sequence to interrupt the reading frame and produce a garbled downstream protein. Such stop or frameshift mutations can be introduced to determine the effect of knocking out the protein in either plant or animal cells. Desirable phenotypes that may be obtained in plants by known nucleic acid sequence alterations include, for example, herbicide resistance; male- or female-sterility; salt, drought, lead, freezing and other stress tolerances; altered amino acid content; altered levels or composition of starch; and altered levels or composition of oils. See, for example, International Patent Application No. PCT/US01/17672, filed Jun. 1, 2001.

Animal or plant genotypes comprising altered levels or activity of at least one protein in the RAD52 epistasis group, the mismatch repair group or the nucleotide excision repair group are another aspect of the invention. Such animals or plants are particularly suitable for directed nucleic acid sequence alteration according to the methods of the invention and can be maintained as a useful genetic stock. The alteration in the at least one protein in the RAD52 epistasis group, the mismatch repair group or the nucleotide excision repair group will then be maintained in the genome after introducing the desired nucleic acid sequence alteration. Optionally, the alteration in the levels or activity of at least one protein in the RAD52 epistasis group, the mismatch repair group or the nucleotide excision repair group may, for example, be removed at the time of the nucleic acid sequence alteration; removed subsequent to the nucleic acid sequence alteration; or removed by conventional breeding.

A further embodiment of the invention is an assay to identify activators of a protein encoded by a RAD10, RAD51, RAD52, RAD54, RAD55, MRE11, PMS1 or XRS2 gene or activators of RAD10, RAD51, RAD52, RAD54, RAD55, MRE11, PMS1 or XRS2 gene expression. As used herein, an activator is a substance which activates (e.g. induces, enhances, increases) expression of a protein or which activates (e.g. induces, enhances, increases) the ability of a protein to enhance nucleic acid sequence alteration efficiency. Such assay methods comprise contacting a sample with an oligonucleotide in a system known to provide for nucleic acid seuquence alteration and measuring whether the amount of nucleic acid sequence alteration is less, more, or the same as in the absence of sample. Many suitable assay systems will be apparent to one of skill in the art, including antibiotic resistance (e.g. tetracycline, kanamycin or hygromycin), GFP and FlAsH systems disclosed herein and in International Patent Application No. PCT/US01/09761.

Another embodiment of the invention is a kit for identifying optimum genetic background for nucleic acid sequence alteration of a particular target. Such a kit may comprise a nucleic acid sequence altering oligonucleotide and one or more cells or cell-free extracts as described for use in the methods of the invention. In a preferred embodiment, a kit for identifying the optimum genetic background for mutagenizing a particular target comprises a collection of cell strains with increased expression or activity of each of the RAD10, RAD51, RAD52, RAD54, RAD55, MRE11, PMS1 or XRS2 genes or combinations thereof. Cells for use in the kits of the invention include cells from any organism including bacteria, fungi, plants, and animals, including humans or other mammals. Cells for use in the kits of the invention include, for example, cultured cells of human liver, lung, colon, cervix, kidney, epithelium, COS-1 and COS-7 cells (African green monkey), CHO-K1 cells (Chinese hamster ovary), H1299 cells (human epithelial carcinoma, non-small cell lung cancer), C127I (immortal murine mammary epithelial cells), MEF (mouse embryonic fibroblasts), HEC-1-A (human uterine carcinoma), HCT15 (human colon cancer), HCT116 (human colon carcinoma), LoVo (human colon adenocarcinoma), and HeLa (human cervical carcinoma) cancer cells as well as PG12 cells (rat pheochromocytoma) and ES cells (human embryonic stem cells). Other stem cell lines that may be used include, for example, any human stem cell line that meets United States federal funding criteria; the National Institutes of Health is currently compiling a list of these existing stem cell lines (http://escr.nih.gov) which includes those held by the following: BresaGen, Inc., Athens, Ga. (4 lines); CyThera, Inc., San Diego, Calif. (9 lines); Karolinska Institute, Stockholm, Sweden (5 lines); Monash University, Melbourne, Australia (6 lines); National Center for Biological Sciences, Bangalore, India (3 lines); Reliance Life Sciences, Mumbai, India (7 lines); Technion-Israel Institute of Technology, Haifa, Israel (4 lines); University of California, San Francisco, Calif. (2 lines); Göteborg University, Göteborg, Sweden (19 lines); Wisconsin Alumni Research Foundation, Madison, Wis. (5 lines). In other embodiments the cells for use in the kits of the invention can be yeast or other fungal cells, or cells from a plant, including, for example, maize, rice, wheat, barley, soybean, cotton, and potato. Other example plants include those described elsewhere herein.

Another embodiment of the invention is a kit for mutagenesis comprising a cell or a cell-free extract enriched for at least one protein or protein activity, the protein encoded by a RAD10, RAD51, RAD52, RAD54, RAD55, MRE11, PMS1 or XRS2 gene. Enrichment of the at least one protein or protein activity can be achieved by any method known in the art or described herein including, for example, supplementation with a purified or partially purified preparation from an organism with extra expression or activity of at least one protein from the group consisting of the RAD10, RAD51, RAD52, RAD54, RAD55, MRE11, PMS1 or XRS2 genes; purifying the cell-free extract from a wild-type organism and subsequently supplementing with at least one additional purified protein; or supplementing the extract with at least one activator of at least one expressed gene product from the group consisting of the RAD10, RAD51, RAD52, RAD54, RAD55, MRE11, PMS1 or XRS2 gene. The cell or cell-free extract for the kit of the invention may be derived from any organism and may be supplemented with a protein or preparation from the same organism or from a different organism. In some embodiments, the cell or cell-free extract is or is from a eukaryotic cell or tissue. In particular embodiments the cell or cell-free extract is or is from a yeast cell.

EXAMPLE 1

DNA Repair Genes Influence the Ability to Direct Nucleic Acid Sequence Alteration In Vitro In this example, we use single-stranded oligonucleotides with modified backbones or double-hairpin oligonucleotides with chimeric, RNA-DNA backbones to measure nucleic acid sequence alteration of episomal target sequences in cell-free extracts from cells with increased or decreased expression of DNA repair genes. These target sequences encode, for example, a kanamycin resistance gene (pKan$^s$m4021), a tetracycline resistance gene, and a fusion between a hygromycin resistance gene and eGFP. In each case, the target gene is non-functional due to at least one point mutation in the coding region.

Preparation and use of cell-free extracts for nucleic acid sequence alteration experiments. We grow yeast cells into log phase ($OD_{600}$=0.5–0.8) in 2L YPD medium at 30° C. We then centrifuge the cultures at 5000×g, resuspend the pellets in a 10% sucrose, 50 mM Tris, 1 mM EDTA lysis solution and freeze them on dry ice. After thawing, we add KCl, spermidine and lyticase to final concentrations of 0.25 mM, 5 mM and 0.1 mg/ml, respectively. We incubate the suspension on ice for 60 minutes, add PMSF and Triton X100 to final concentrations of 0.1 mM and 0.1% and continue to incubate on ice for 20 minutes. We centrifuge the lysate at 3000×g for 10 minutes to remove larger debris. We then remove the supernatant and clarify it by centrifuging at 30000×g for 15 minutes. We then add glycerol to the clarified extract to a concentration of 10% (v/v) and freeze aliquots at −80° C. We determine the protein concentration of the extract by the Bradford assay.

To assay nucleic acid sequence alteration activity, we use 50 μl reaction mixtures comprising 10–30 μg protein of cell-free extract from either a wild-type yeast strain or a yeast strain having a mutation in a gene from the RAD52 epistasis group, the mismatch repair group or the nucleotide excision repair group; about 1.5 μg chimeric double-hairpin oligonucleotide (KanGG, see FIG. 1) or 0.55 μg single-stranded molecule (3S/25G or 6S/25G, 25-mer oligonucleotides directing the same alteration as KanGG and having 3 or 6 phosphorothioate linkages at each end, respectively); and about 1 μg of plasmid DNA (see FIG. 1) in a reaction buffer comprising 20 mM Tris pH 7.4, 15 mM $MgCl_2$, 0.4 mM DTT, and 1.0 mM ATP. We initiate the reactions by adding cell-free extract and incubating at 30° C. for 45 min. We stop the reaction by placing the tubes on ice and then immediately deproteinize them with two phenol/chloroform (1:1) extractions. We then ethanol precipitate the samples and pellet the nucleic acid at 15,000 r.p.m. at 4° C. for 30 min; wash the pellet with 70% ethanol; resuspend the nucleic acid in 50 μl $H_2O$; and store it at −20° C.

We measure the effect of oligonucleotide concentration on nucleic acid sequence alteration in cell-free extract as follows. We use about 1 μg of plasmid pK$^s$m4021 and varying amounts of oligonucleotide in a 100 μl reaction mixtures comprising 20 mM Tris pH 7.6; 15 mM $MgCl_2$; 1 mM DTT; 0.2 mM spermidine; 2.5 mM ATP; 0.1 mM each CTP, GTP, UTP; 0.01 mM each dATP, dCTP, dGTP and dTTP; 0.1 mM NAD; and 10 μg/ml BSA. We start the reactions by adding 10–80 μg of cell-free extract and incubate the reactions at 30° C. for 30 min. We stop the reactions on ice and isolate the plasmid DNA with two phenol and one chloroform extraction followed by ethanol precipitation on dry ice for 1 hr and centrifugation at 4° for 30 min. We then wash the pellet with 70% ethanol, resuspend in 50 μl $H_2O$ and store at −20° C.

Quantification of nucleic acid sequence alteration. We then electroporate 5 μl of plasmid from the resuspension (~100 ng) into 20 μl of DH10B cells in a Cell-Porator apparatus with settings of 400 V, 300 μF, 4 kΩ (Life Technologies). After electroporation, we transfer cells to a 14 ml Falcon snap-cap tube with 1 or 2 ml SOC and shake at 37° C. for 1 h. To enhance the final kanamycin resistant colony counts, we amplify plasmids with altered sequence by adding kanamycin (50 μg/ml) or 3 ml SOC with 10 μg/ml kanamycin and shake the cell suspension for 2 or 3 h more at 37° C. We then directly plate 100 μl aliquots of undiluted cultures on LB agar plates with 50 mg/ml kanamycin and 100 μl aliquots of a $10^4$ dilution on LB agar plates with 100 mg/ml ampicillin. Alternatively, we first centrifuge the cells at 3750×g and resuspend the pellet in 500 μl SOC. We add 200 μl of the resuspension (undiluted) to kanamycin (50 μg/ml) agar plates and 200 μl of a $10^5$ dilution to ampicillin (100 μg/ml) plates. After overnight 37° C. incubation, we count bacterial colonies using an Accucount 1000 (Biologics). We measure nucleic acid sequence alteration efficiency as the ratio of the kanamycin resistant colonies to the ampicillin resistant colonies corrected for the dilution.

Alternatively, we use the following procedure. We transform 5 μl of resuspended reaction mixtures (total volume 50

μl) into 20 μl aliquots of electro-competent DH10B bacteria using a Cell-Porator apparatus (Life Technologies). We allow the mixtures to recover in 1 ml SOC at 37° C. for 1 hour at which time we add 50 μg/ml kanamycin or 12 μg/ml tetracycline (for kanamycin or tetracycline plasmids, respectively) and incubate for an additional 3 hours. Prior to plating, we pellet the bacteria and resuspend in 200 μl of SOC. We plate 100 μl aliquots on kanamycin or tetracycline agar plates and 100 μl of a $10^{-4}$ dilution of the cultures on agar plates containing 100 μg/ml of ampicillin. We determine colony counts using an Accu-count 1000 plate reader (Biologics).

For both plating procedures we generally plate in duplicate or triplicate. Each plate contains 200–500 ampicillin resistant colonies or 0–500 tetracycline or kanamycin resistant colonies. We then select resistant colonies for plasmid isolation and DNA sequencing using an ABI Prism kit on an ABI 310 capillary sequencer (PE Biosystems).

Nucleic acid sequence alteration in cell-free extracts from yeast. We use the kanamycin plasmid assay system to test cell-free extracts from the yeast strain LSY678. As shown in Table 1, we observe that the reaction depends on all reaction components. We also generally observe that increasing the amount of oligonucleotide or the amount of extract in the reaction increases the relative alteration efficiency. We then analyze the efficiency of nucleic acid sequence alteration in yeast strains deficient for at least one protein from the RAD52 epistasis group, the mismatch repair group or the nucleotide excision repair group. We find that extracts produced from an msh2 mutant yeast strain (LSY814) show a significant reduction in repair activity similar to the lower gene repair that we see in mammalian cells deficient in MSH2p (Table 2). We observe that cell-free extracts from rad57 or rad59 mutant strains lacking show little change in nucleic acid sequence alteration activity and that cell free extracts from rad23 or rad54 mutant strains show a slight increase in nucleic acid sequence alteration activity relative to a strain with functional copies of these genes. However, we observe elevated nucleic acid sequence alteration frequencies using cell-free extracts from rad51 or rad52 mutant strains. In particular, we observe that the Δrad52 (LSY386) strain exhibits about 5-fold to about 25-fold higher repair frequency. In all samples, the range of ampicillin resistance colonies is 500–600 per plate with kanamycin colonies between 10 and 300.

Gene repair depends on the dose of repair proteins. We examine the activity of an extract lacking RAD52 in more detail. First, we observe that repair of pK$^s$m4021 depends on the addition of all three components: plasmid, oligonucleotide and extract (Table 3). We also observe that the repair is dose-dependent and proportional to the amount of LSY386 (Δrad52) extract present in a reaction where two extracts are mixed (Table 3). We confirm that RAD52 is present in these extracts by western blot analyses. We observe a similar effect on repair in cell-free extract when a rad52 mutant strain lacking RAD52 is mixed with a rad23 mutant strain (YELO37C) instead of LSY678.

Finally, we analyze nucleic acid sequence alteration efficiency of cell-free extracts from LSY386 or LSY678 containing a plasmid expressing RAD52. We observe that the expression of RAD52 reduces the level of nucleic acid sequence alteration activity in extracts made from either LSY386 or LSY678. In LSY386, the level of repair drops to near wild-type levels while the level in LSY678 is reduced to 4-fold below wild-type levels (Table 3). We perform western blot analysis on these strains and the level of RAD52 protein expression in these strains is approximately equal. These results indicate that expression of the RAD52 gene suppresses oligonucleotide-directed nucleic acid sequence alteration. We also analyze the DNA sequence of the target plasmid from three colonies and observe that the targeted base is precisely changed even in samples in which the extract came from Δrad51 or Δrad23. Hence, target specificity is maintained despite the mutations and the differences in nucleic acid sequence alteration frequency.

Tables are attached hereto.

TABLE 1

Gene repair using *Saccaromyces cerevisae* extracts

| Plasmid (1 μg) | Chimeric Oligonucleotide (μg) | Extract (μg) | Relative Frequency kan$^r$/amp$^r$(×$10^{-5}$) |
|---|---|---|---|
| pK$^s$m4021 | 1 (Kan GG) | — | 0.002 |
| pK$^s$m4021 | — | 20 | 0.0 |
| — | 1 (Kan GG) | 20 | 0.0 |
| — | — | — | 0.0 |
| pK$^s$m4021 | 1 (Kan GG) | 1 | 0.32 |
| pK$^s$m4021 | 1 (Kan GG) | 10 | 3.66 |
| pK$^s$m4021 | 1 (Kan GG) | 20 | 7.601 |
| pK$^s$m4021 | 0.5 (Kan GG) | 10 | 1.89 |
| pK$^s$m4021 | 1.0 (Kan GG) | 10 | 2.78 |
| pK$^s$m4021 | 2.0 (Kan GG) | 10 | 4.005 |
| pK$^s$m4021 | 1 (Kan CG) | — | 0.0 |
| pK$^s$m4021 | 1 (Kan CG) | 20 | 0.003 |

Chimeric oligonucleotides at varying levels are incubated with plasmid pK$^s$m4021 and the indicated amounts of cell-free extracts from *Saccharomyces cerevisae* (LSY678) for 45 minutes at 30° C. We isolate, purify and electroporate the plasmids into *E. coli* (DH10B) and quantify resistant colonies using an automatic plate reader. Relative frequency is presented as kanamycin resistant colonies divided by ampicillin resistant colonies (×$10^{-5}$). Oligonucleotide KanCG has the same sequence as KanGG except there is no mismatch and KanCG does not correct the mutation. Each data point is presented as the average of 5 independent experiments.

TABLE 2

Gene repair using mutant strains of *Saccaromyces cerevisae*

| Plasmid | Oligonucleotide | Source of Extract | Relative Alteration Efficiency |
|---|---|---|---|
| pK$^s$m4021 | KanGG | — | 0.0 |
| pK$^s$m4021 | — | LSY678 | 0.002 |
| pK$^s$m4021 | KanGG | LSY678 (wild type) | 1.17 |
| pK$^s$m4021 | KanGG | LSY814 (Δmsh2) | 0.79 |
| pK$^s$m4021 | KanGG | LSY402 (Δrad51) | 5.15 |
| pK$^s$m4021 | KanGG | LSY386 (Δrad52) | 25.7 |
| pK$^s$m4021 | KanGG | XS827-18C (Δrad54) | 1.36 |
| pK$^s$m4021 | KanGG | YDR076W (Δrad55) | 1.27 |
| pK$^s$m4021 | KanGG | LSY407 (Δrad57) | 2.13 |
| pK$^s$m4021 | KanGG | LSY837 (Δrad59) | 0.35 |
| pK$^s$m4021 | KanGG | YELO37C (Δrad23) | 1.04 |

Reaction mixtures (20 μl) containing 1 μg plasmid pK$^s$m4021 and 1 μg oligonucleotide KanGG are mixed with 10 μg of a cell-free extract from the indicated yeast strains. After a 45 minute incubation at 30° C., we isolate the plasmid DNA and electroporate into *E. coli* (DH10B). We count kanamycin resistant colonies on agar plates containing 50 μg/ml kanamycin. Plasmids from duplicate reaction mixtures are also electroporated into *E. coli* (DH10B) and plated on ampicillin containing plates. We determine relative activity by dividing Kan$^r$ by Amp$^r$ colony numbers. These numbers reflect an average of five reactions.

TABLE 3

Extracts from LSY386(Δrad52) exhibit higher levels of gene repair

| Plasmid | Oligo-nucleotide | Source of First Extract | Source of Second Extract | Relative Alteration Efficiency |
|---|---|---|---|---|
| pK$^S$m4021 | — | — | — | 0.0 |
| — | KanGG | — | — | 0.0 |
| pK$^S$m4021 | KanGG | — | — | 0.003 |
| pK$^S$m4021 | KanGG | LSY678 (wild type) | — | 1.08 |
| pK$^S$m4021 | KanGG | LSY386 (Δrad52) | — | 26.7 |
| pK$^S$m4021 | KanGG | LSY386(2 μg) | LSY678(8 μg) | 2.91 |
| pK$^S$m4021 | KanGG | LSY386(4 μg) | LSY678(6 μg) | 5.45 |
| pK$^S$m4021 | KanGG | LSY386(6 μg) | LSY678(4 μg) | 10.47 |
| pK$^S$m4021 | KanGG | LSY386(8 μg) | LSY678(2 μg) | 14.36 |
| pK$^S$m4021 | KanGG | LSY386(2 μg) | YELO37C(8 μg) | 1.85 |
| pK$^S$m4021 | KanGG | LSY386(4 μg) | YELO37C(6 μg) | 3.71 |
| pK$^S$m4021 | KanGG | LSY386(6 μg) | YELO37C(4 μg) | 9.22 |
| pK$^S$m4021 | KanGG | LSY386(8 μg) | YELO37C(2 μg) | 16.95 |
| pK$^S$m4021 | KanGG | LSY386 | — | 19.9 |
| pK$^S$m4021 | KanGG | LSY386 · p52 | — | 2.31 |
| pK$^S$m4021 | KanGG | LSY678 | — | 1.63 |
| pK$^S$m4021 | KanGG | LSY678 · p52 | — | 0.41 |

Reaction mixtures and processing for colonies are as described in the legend to Table 1 with the following exceptions. We use cell-free extracts from yeast strains containing mutations as follows: LSY678 (wild type), LSY386 (Δrad52), and YELO37C (Δrad23). We use either 10 μg of extract or the amounts indicated. The reactions identified as LSY386 · p52 contain a cell-free extract from a Δrad52 strain (LSY386) harboring a plasmid which expresses RAD52 protein. The reactions identified as LSY678 · p52 contain a cell-free extract from wild-type strain (LSY678) harboring a plasmid which expresses RAD52 protein.

EXAMPLE 2

DNA Repair Genes Influence the Ability to Direct Nucleic Acid Sequence Alteration In Vivo In this example, we use single-stranded oligonucleotides with modified backbones or double-hairpin oligonucleotides with chimeric, RNA-DNA backbones to measure nucleic acid sequence alteration of target sequences in cells with increased or decreased expression of DNA repair genes. These target sequences encode, for example, a fusion between a hygromycin resistance gene and eGFP which is non-functional due to at least one point mutation in the coding region. The target sequences may be either episomal or chromosomal (including, e.g., nuclear, mitochondrial or plastidic). Nucleic acid sequence alteration of episomal targets is generally slightly more efficient (less than twofold) than nucleic acid sequence alteration of chromosomal targets. Modifications to the oligonucleotides and construction of target vectors are disclosed in the copending International Patent Application PCT/US01/09761 of Kmiec et al. entitled "Targeted Chromosomal Genomic Alterations with Modified Single Stranded Oligonucleotides," filed Mar. 27, 2001, the disclosure of which is hereby incorporated by reference.

Figure 2:
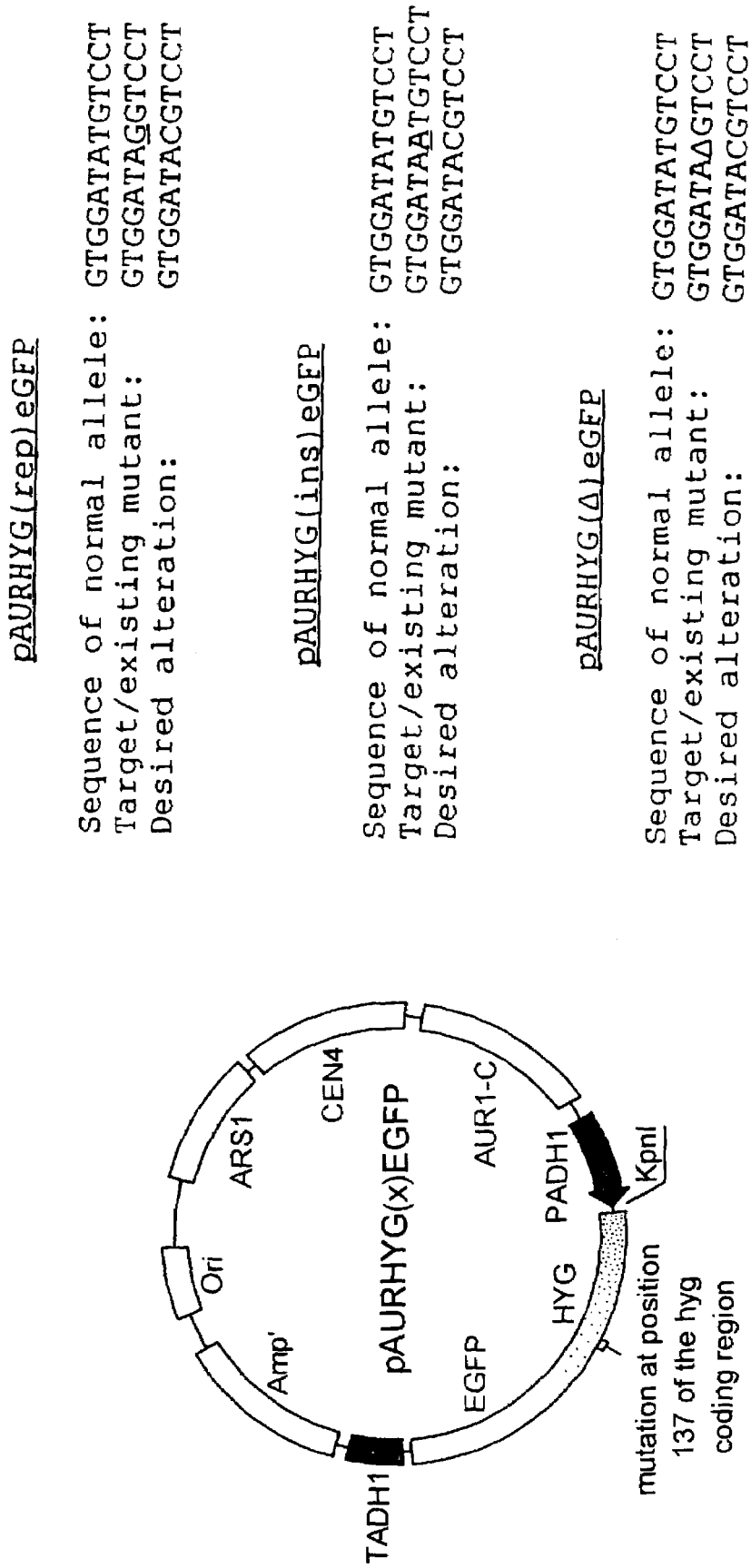
FIG. 2. Hygromycin-eGFP target plasmids. Diagram of plasmid pAURHYG(x)eGFP. Plasmid pAURHYG(rep) eGFP contains a base substitution mutation introducing a G at nucleotide 137, at codon 46, of the Hygromycin B coding sequence (cds). Plasmid pAURHYG(ins)eGFP contains a single base insertion mutation between nucleotides 136 and 137, at codon 46, of the Hygromycin B coding sequence (cds) which is transcribed from the constitutive ADH1 promoter. Plasmid pAURHYG(Δ)eGFP contains a deletion mutation removing a single nucleotide at codon 46, of the Hygromycin B coding sequence (cds). The target sequence presented below indicates the deletion of an A and the substitution of a C for a T directed by the oligonucleotides to re-establish the resistant phenotype. The target sequence presented below the diagram indicates the amino acid conservative replacement of G with C, restoring gene function. The sequences of the normal hygromycin resistance allele (SEQ ID NO: 2) and the desired allele after nucleic acid sequence alteration (SEQ ID NO: 3) are shown next to the mutant alleles present in pAURHYG(rep)eGFP (SEQ ID NO: 4), pAURHYG(ins)eGFP (SEQ ID NO: 5) and pAURHYG(Δ)eGFP (SEQ ID NO: 6). The position of the deletion in the pAURHYG(Δ)eGFP allele is indicated with the symbol Δ.

In vivo assay systems. To monitor nucleic acid sequence alteration of episomal targets, we employ a yeast system using the plasmids pAURHYG(rep)eGFP, which contains a point mutation in the hygromycin resistance gene, pAURHYG(ins)eGFP, which contains a single-base insertion in the hygromycin resistance gene and pAURHYG(Δ)eGFP which has a single base deletion (shown in FIG. 2). We also use the same plasmid containing a functional copy of the hygromycin-eGFP fusion gene, designated pAURHYG(wt)eGFP, as a control. These plasmids are collectively designated pAURHYG(x)eGFP. These plasmids also contain an aureobasidinA resistance gene. In pAURHYG(rep)eGFP, hygromycin resistance gene function and green fluorescence from the eGFP protein are restored when a G at position 137, in codon 46 of the hygromycin B coding sequence, is converted to a C thus removing a premature stop codon in the hygromycin resistance gene coding region. In pAURHYG(ins)eGFP, hygromycin resistance gene function and green fluorescence from the eGFP protein are restored when an A inserted between nucleotide positions 136 and 137, in codon 46 of the hygromycin B coding sequence, is deleted and a C is substituted for the T at position 137, thus correcting a frameshift mutation and restoring the reading frame of the hygromycin-eGFP fusion gene. In pAURHYG(Δ)eGFP, hygromycin resistance gene function and green fluorescence from eGFP are restored when a C is inserted at the site of the single nucleotide deletion.

We synthesize the set of three yeast expression constructs pAURHYG(rep)eGFP, pAURHYG(Δ)eGFP, pAURHYG(ins)eGFP, that contain a point mutation at nucleotide 137 of the hygromycin-B coding sequence as follows: (rep) indicates a T137→G replacement, (Δ) represents a deletion of G137 and (ins) represents an A insertion between nucleotides 136 and 137. We construct this set of plasmids by excising the respective expression cassettes by restriction digest from pHyg(x)eGFP and ligation into pAUR123 (PanVera, Calif.). We digest 10 μg pAUR123 vector DNA as well as 10 μg of each pHyg(x)EGFP construct with KpnI and SalI (NEB). We gel purify each of the DNA fragments and prepare them for enzymatic ligation. We ligate each mutated insert into pAUR123 vector at a 3:1 molar ratio using T4 DNA ligase (Roche). We screen clones by restriction digest, confirm by Sanger dideoxy chain termination sequencing and purify plasmid DNA using a Qiagen maxiprep kit.

To monitor nucleic acid sequence alteration of chromosomal targets, we typically employ a yeast system in which we monitor chromosomal genes such as CYC1 or we use integrational plasmids such as those designated pAUR101-HYG(x)eGFP. These plasmids do not replicate in yeast. These plasmids comprise the HYG(x)eGFP fusion proteins used in the pAURHYG(x)eGFP episomal plasmid system (shown in FIG. 2) and an aureobasidinA resistance gene. Therefore, like pAURHYG(x)eGFP, these constructs can also be used to monitor all types of sequence alterations, i.e. replacements, insertions and deletions. In addition to this construct, we monitor nucleic acid sequence alteration of specific yeast genes including, for example, CYC1.

Figure 8A:
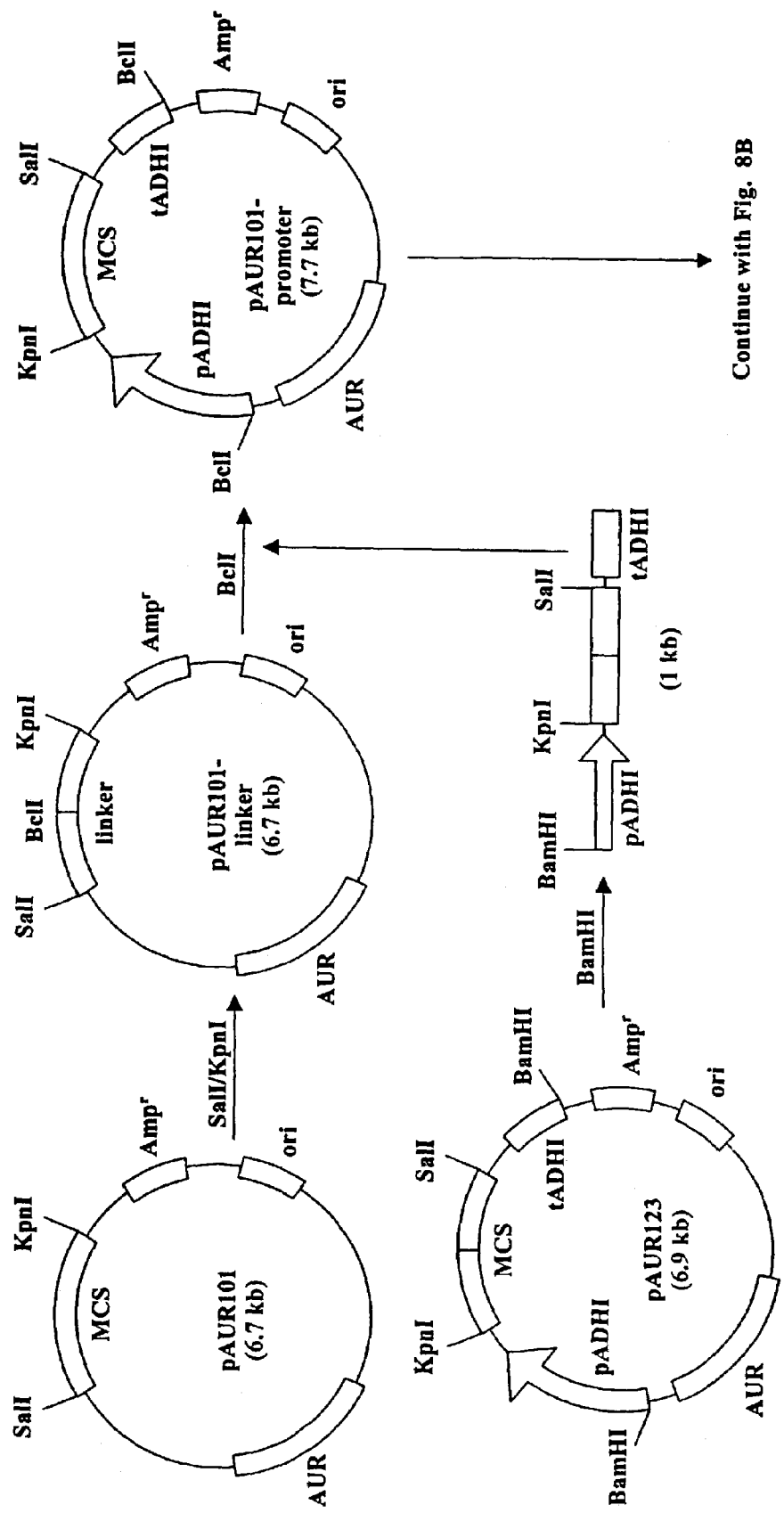
FIGS. 8A and 8B. Construction of pAUR101-HYG(x) eGFP plasmid. This figure diagrams the construction scheme for the pAUR101-HYG(x)eGFP integrational plasmid.
Figure 8B:
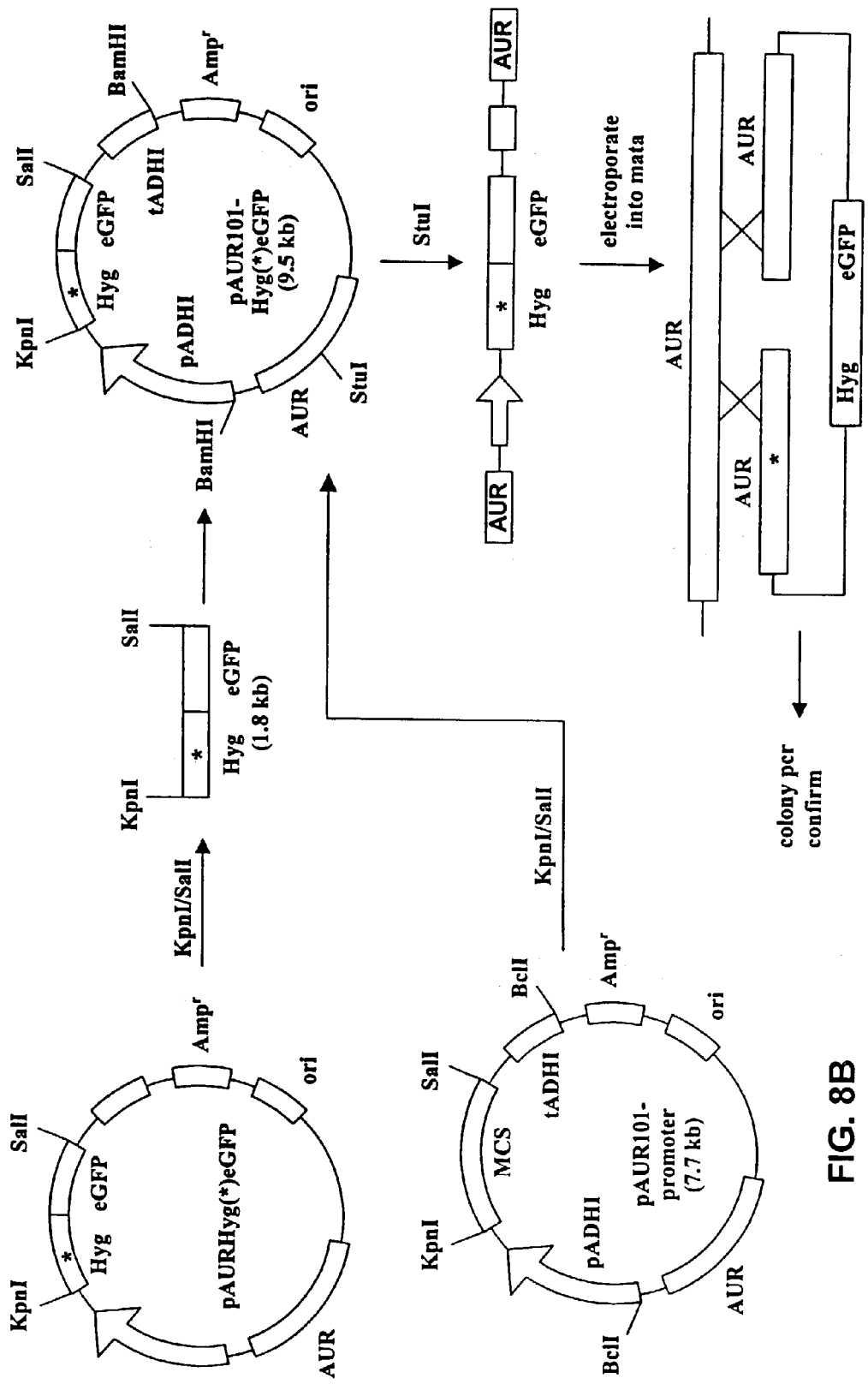

We construct the pAUR101-HYG(x)eGFP plasmids as diagrammed in FIG. 8. Briefly, we digest 10 μg pAUR101 (PanVera Corp.) with SalI and KpnI and ligate a linker comprising a unique BclI restriction site. We then digest 10 μg of the resulting plasmid ("pAUR101-linker") with BclI and ligate in a 1 kb BamHI fragment from pAUR123. The BamHI fragment from pAUR123 comprises a multiple-cloning site as well as the ADH1 promoter and terminator regions. We then digest 10 μg of this plasmid ("pAUR101-promoter") with SalI and KpnI and ligate in a 1.8 kb SalI/KpnI fragment from pAURHYG(x)eGFP which contains the HYG(x)eGFP fusion protein. The resulting plasmid is pAUR101-HYG(x)eGFP. All DNA fragments are gel purified after restriction enzyme digestion to prepare them for enzymatic ligation. All ligations are performed using T4 DNA ligase (Roche). Clones are screened by restriction digest and confirmed by Sanger dideoxy chain termination sequencing.

We integrate the plasmids into the genome of wild-type yeast cells as well as yeast strains with mutations in a variety of genes, including, for example, genes of the RAD52 epistasis group, the mismatch repair group and the nucleotide excision repair group. We integrate the plasmids into the yeast genome by linearizing 10 µg of the plasmid by digestion with StuI and electroporating the linearized plasmid into the yeast cells. The plasmid integrates by homologous recombination at the wild-type AUR-C (aureobasidinA) locus. We then select on aureobasidinA to identify clones in which the plasmid has integrated. We confirm that the plasmid has integrated by PCR analysis and by performing Southern blots. We obtain yeast strains with single as well as multiple integrated copies of the plasmid.

We also synthesize a set of yeast expression plasmids to express genes from the RAD52 epistasis group, the mismatch repair group and the nucleotide excision repair group. We use the plasmid pYN132 which has the promoter from the TPL1 gene, which directs high-level constitutive expression of genes cloned downstream (Alber et al. *J. Mol. Appl. Genet.* 1: 419–34 (1982)). We construct the expression plasmids by digesting 10 µg pYN132 DNA as well as 10 µg of a PCR product containing one of the DNA repair protein with NdeI and XhoI (NEB). We gel purify each of the DNA fragments and prepare them for ligation. We ligate the PCR product into the pYN132 vector at a 3:1 molar ratio using T4 DNA ligase (Roche). We screen clones by restriction digest, confirm the clone by Sanger dideoxy chain termination sequencing and purify plasmid DNA using a Qiagen maxiprep kit.

We use this system to assay the ability of modified oligonucleotides (shown in FIG. 3) to support nucleic acid sequence alteration in a variety of host cell backgrounds including wild-type, mutants and cells expressing additional gene(s). We also use this system with chimeric RNA-DNA double-hairpin oligonucleotides. These oligonucleotides direct alteration of the mutation in pAURHYG(rep)eGFP as well as the mutation in pAURHYG(ins)eGFP or pAURHYG(Δ)eGFP. The first of these oligonucleotides, HygE3T/74, is a 74-base oligonucleotide with the sequence directing nucleic acid sequence alteration centrally positioned. The second oligonucleotide, designated HygE3T/74NT, is the reverse complement of HygE3T/74. The third oligonucleotide, designated Kan70T, is a non-specific, control oligonucleotide which is not complementary to the target sequence. Alternatively, an oligonucleotide of identical sequence but lacking a mismatch to the target or a completely phosphorothioate-modified oligonucleotide or a completely 2-O-methylated modified oligonucleotide may be used as a control.

Oligonucleotide synthesis and cells. We synthesize and purify the oligonucleotides using available phosphoramidites on controlled pore glass supports. After deprotection and detachment from the solid support, each oligonucleotide is gel-purified using, for example, procedures such as those described in Gamper et al., *Biochem.* 39, 5808–5816 (2000). We determine the concentration of the oligonucleotides spectrophotometrically (33 or 40 µg/ml per $A_{260}$ unit of single-stranded or hairpin oligomer, respectively). Plasmids used for assay are maintained stably at low copy number under aureobasidin selection in yeast (*Saccharomyces cerevisiae*) strain LSY678 (wild type) which optionally may contain additional gene mutations or may be engineered to express additional protein(s).

Plasmids and oligonucleotides are introduced into yeast cells by electroporation as follows: to prepare electrocompetent yeast cells, we inoculate 10 ml of YPD media from a single colony and grow the cultures overnight with shaking at 300 rpm at 30° C. We then add 30 ml of fresh YPD media to the overnight cultures and continue shaking at 30° C. until the $OD_{600}$ was between 0.5 and 1.0 (3–5 hours). We then wash the cells by centrifuging at 4° C. at 3000 rpm for 5 minutes and twice resuspending the cells in 25 ml ice-cold distilled water. We then centrifuge at 4° C. at 3000 rpm for 5 minutes and resuspend in 1 ml ice-cold 1M sorbitol and then finally centrifuge the cells at 4° C. at 5000 rpm for 5 minutes and resuspend the cells in 120 µl 1M sorbitol. To transform electrocompetent cells with plasmids or oligonucleotides, we mix 40 µl of cells with 5 µg of nucleic acid, unless otherwise stated, and incubate on ice for 5 minutes. We then transfer the mixture to a 0.2 cm electroporation cuvette and electroporate with a BIO-RAD Gene Pulser apparatus set at 1.5 kV, 25 µF, 200 Ω for one five-second pulse. We then immediately resuspend the cells in 1 ml YPD supplemented with 1M sorbitol and incubate the cultures at 30° C. with shaking at 300 rpm for 6 hours. We then spread 200 µl of this culture on selective plates containing 300 µg/ml hygromycin and spread 200 µl of a $10^5$ dilution of this culture on selective plates containing 500 ng/ml aureobasidinA and/or hygromycin and incubate at 30° C. for 3 days to allow individual yeast colonies to grow. We then count the colonies on the plates and calculate the nucleic acid sequence alteration efficiency by determining the number of hygromycin resistance colonies per $10^5$ aureobasidinA resistant colonies.

Nucleic acid sequence alteration to repair different mutations in wild-type *Saccharomyces cerevisiae*. We test the ability of oligonucleotides shown in FIG. 3 to alter all three target plasmids in vivo using wild-type yeast strain LSY678. These target plasmids contain a point mutation (pAURHYG (rep)eGFP), a deletion mutation (pAURHYG(Δ)eGFP) or an insertion mutation (pAURHYG(ins)eGFP). We also test oligonucleotides targeting opposite strands of the target DNA to identify any strand-specific effects and we test the oligonucleotide at a range of concentration to determine the optimum concentration for gene repair.

As shown in Table 4, we observe that oligonucleotides targeting either strand direct alteration of all three types of mutations. The data indicate that the point mutation in pAURHYG(rep)eGFP is corrected more efficiently than the insertion mutation in pAURHYG(ins)eGFP, which in turn is corrected more efficiently than the deletion mutation in pAURHYG(Δ)eGFP. In addition, with all three assay plasmids we observe that the optimal oligonucleotide concentration for nucleic acid sequence alteration in this system is 5 µg. We note, however, that the oligonucleotides are capable of effecting repair over a wide range of concentrations. Finally, we observe that the oligonucleotide with sequence complementary to the sense strand of the target DNA, HygE3T/74NT, repairs all three types of target mutations more effectively than the complementary oligonucleotide, HygE3T/74. The fold difference in repair efficiency using HygE3T/74NT relative to using HygE3T/74 is indicated in the final column of Table 4.

Figure 3:
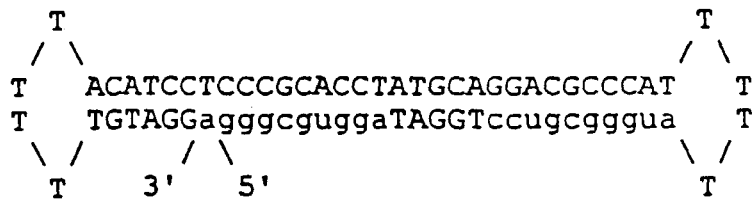
FIG. 3. Oligonucleotides for alteration of hygromycin resistance gene. The sequence of the oligonucleotides used in experiments to assay alteration of a hygromycin resistance gene are shown. DNA residues are shown in capital letters, RNA residues are shown in lowercase and nucleotides with a phosphorothioate backbone are capitalized and underlined.

We also test the ability of oligonucleotides shown in FIG. 3 to alter all three target mutations in strains comprising the integrated pAUR101-HYG(x)eGFP plasmids. We test multiple concentrations of oligonucleotides targeting either strand of the DNA duplex target. The results of these types of experiments with the replacement mutation in pAUR101-HYG(rep)eGFP are shown in Table 14 including data on how to determine an optimized oligonucleotide concentration. We observe that oligonucleotides targeting either strand direct alteration of the point mutation in the integrated pAUR101-HYG(rep)eGFP plasmid and that the optimal oligonucleotide concentration for nucleic acid sequence alteration with this chromosomal target is 7.5 µg. We note again, however, that the oligonucleotides are capable of effecting repair over a wide range of concentrations. We observe that the oligonucleotide with sequence complementary to the sense strand of the target DNA, HygE3T/74NT, repairs the chromosomal target mutation more effectively than the complementary oligonucleotide, HygE3T/74, at all concentrations tested. The fold difference in alteration efficiency using HygE3T/74NT relative to using HygE3T/74 is indicated in the final column of Table 14.

Nucleic acid sequence alteration in strains with mutation(s) in gene(s) of the RAD52 epistasis group. We test the ability of oligonucleotides shown in FIG. 3 to alter a nucleic acid sequence in vivo using yeast strains with additional mutation(s) in gene(s) of the RAD52 epistasis group. In these experiments we use derivatives of LSY678 (wild type) with a mutation in one or more of the genes of the RAD52 epistasis group and containing the target plasmid pAURHYG(rep)eGFP, pAURHYG(ins)eGFP or pAUR HYG(Δ)eGFP. We electroporate these cells with 5 µg of HygE3T/74 and plate on hygromycin and aureobasidinA to obtain the efficiency of nucleic acid sequence alteration. The results of these experiments for plasmid pAURHYG(rep) eGFP, pAURHYG(ins)eGFP and pAUR HYG(Δ)eGFP are shown in Table 5, Table 6 and Table 7, respectively. We also monitor nucleic acid sequence alteration efficiency on chromosomal targets in yeast strains with mutation(s) in gene(s) of the RAD52 epistasis group.

These data indicate that the efficiency of nucleic acid sequence alteration is changed in a yeast strain with a mutation in RAD51, RAD52, RAD54, RAD55, RAD59, RAD50, MRE11 or XRS2. The efficiency of nucleic acid sequence alteration that we observe in these experiments in strains with mutations in either RAD57 or a double mutant in rad51/52 is reduced when using pAURHYG(ins)eGFP or pAUR HYG(A)eGFP as the target plasmid, but, surprisingly, we observe an increase in the efficiency of nucleic acid sequence alteration in these strains when using pAURHYG (rep)eGFP as the target. We observe that nucleic acid sequence alteration using pAURHYG(rep)eGFP as the target is reduced in yeast strains with mutations in RAD54 or RAD55. We also perform control experiments with LSY678 yeast cells containing the plasmid pAURHYG(wt)eGFP. With this strain we observe that even without added oligonucleotides, there are too many hygromycin resistant colonies to count. We test yeast strains with mutations in both single genes in the RAD52 epistasis group as well as yeast strains with mutations in two or more of the genes. We test the ability of these yeast strains to correct all of the pAURHYG(x)eGFP mutations.

Nucleic acid sequence alteration in strains with mutation(s) in mismatch repair gene(s). We test the ability of oligonucleotides shown in FIG. 3 to alter a nucleic acid sequence in vivo using yeast strains with additional mutation(s) in mismatch repair gene(s) containing the plasmid pAURHYG(x)GFP. We electroporate these cells with 5 µg of HygE3T/74 and plate on hygromycin and aureobasidinA to obtain the efficiency of nucleic acid sequence alteration. For example, the results of these experiments for plasmid pAURHYG(rep)eGFP, pAURHYG(ins)eGFP and pAUR HYG(Δ)eGFP are shown in Table 5, Table 6 and Table 7, respectively. We also monitor nucleic acid sequence alteration efficiency on chromosomal targets in yeast strains with mutation(s) in gene(s) of the RAD52 epistasis group.

These data indicate that nucleic acid sequence alteration occurs at a reduced efficiency in strains with mutations in MSH2, MSH3 or MSH6 and at an increased efficiency in strains with a mutation in PMS1. We observe the same general effects, although at different relative efficiencies, in experiments using either plasmid pAURHYG(rep)eGFP, plasmid pAURHYG(ins)eGFP or pAUR HYG(Δ)eGFP as the target. In control experiments with LSY678 yeast cells containing the plasmid pAURHYG(wt)eGFP, we again observe that, even without added oligonucleotides, there are too many hygromycin resistant colonies to count. We test yeast strains with mutations in both single mismatch repair genes as well as yeast strains with mutations in two or more of the genes. We test the ability of these yeast strains to correct all of the pAURHYG(x)eGFP mutations.

Nucleic acid sequence alteration in strains with mutation(s) in nucleotide excision repair gene(s). We test the ability of oligonucleotides shown in FIG. 3 to alter a nucleic acid sequence in vivo using yeast strains with additional mutation(s) in nucleotide excision repair gene(s) containing the plasmid pAURHYG(x)eGFP. We electroporate these cells with 5 µg of HygE3T/74 and plate on hygromycin and aureobasidinA to obtain the efficiency of nucleic acid sequence alteration. For example, the results of these experiments for plasmid pAURHYG(rep)eGFP, pAURHYG(ins) eGFP and pAUR HYG(Δ)eGFP are shown in Table 5, Table 6 and Table 7, respectively. We also monitor nucleic acid sequence alteration efficiency on chromosomal targets in yeast strains with mutation(s) in gene(s) of the RAD52 epistasis group.

These data indicate that nucleic acid sequence alteration occurs at a reduced efficiency in strains with mutations in RAD10, RAD2, or RAD23. The efficiency of nucleic acid sequence alteration observed in these experiments in a strain with a mutation in RAD1 is reduced when using either pAURHYG(ins)eGFP or pAUR HYG(A)eGFP as the target plasmid, but increased when using pAURHYG(rep)eGFP as the target. We observe that nucleic acid sequence alteration is reduced in a yeast strain with a mutation in EXO1 using pAURHYG(rep)eGFP or pAURHYG(ins)eGFP as the target. We also perform control experiments with LSY678 yeast cells containing the plasmid pAURHYG(wt)eGFP which yield too many hygromycin resistant colonies to count. We test yeast strains with mutations in both single nucleotide excision repair genes as well as yeast strains with mutations in two or more of the genes. We test the ability of these yeast strains to correct all of the pAURHYG(x)eGFP mutations.

Figure 4:
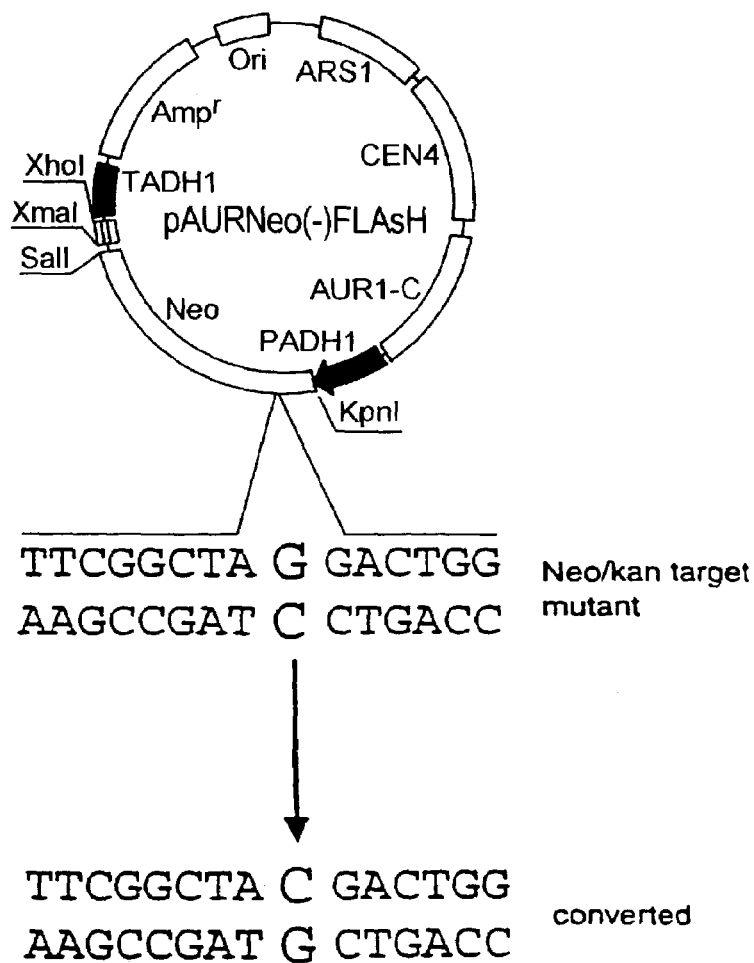
FIG. 4. pAURNeo(−)FlAsH plasmid. This figure describes the plasmid structure, target sequence, oligonucleotides, and the basis for detection of the nucleic acid sequence alteration event by fluorescence.
Figure 4:
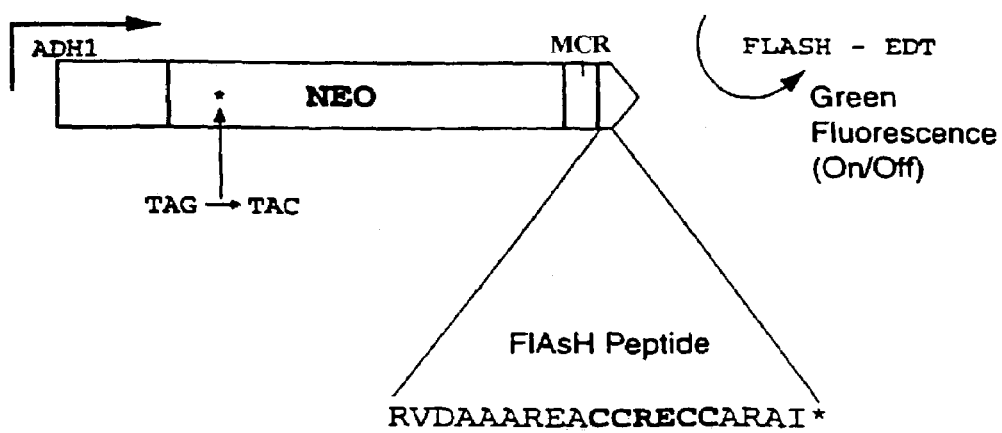
Figure 6:
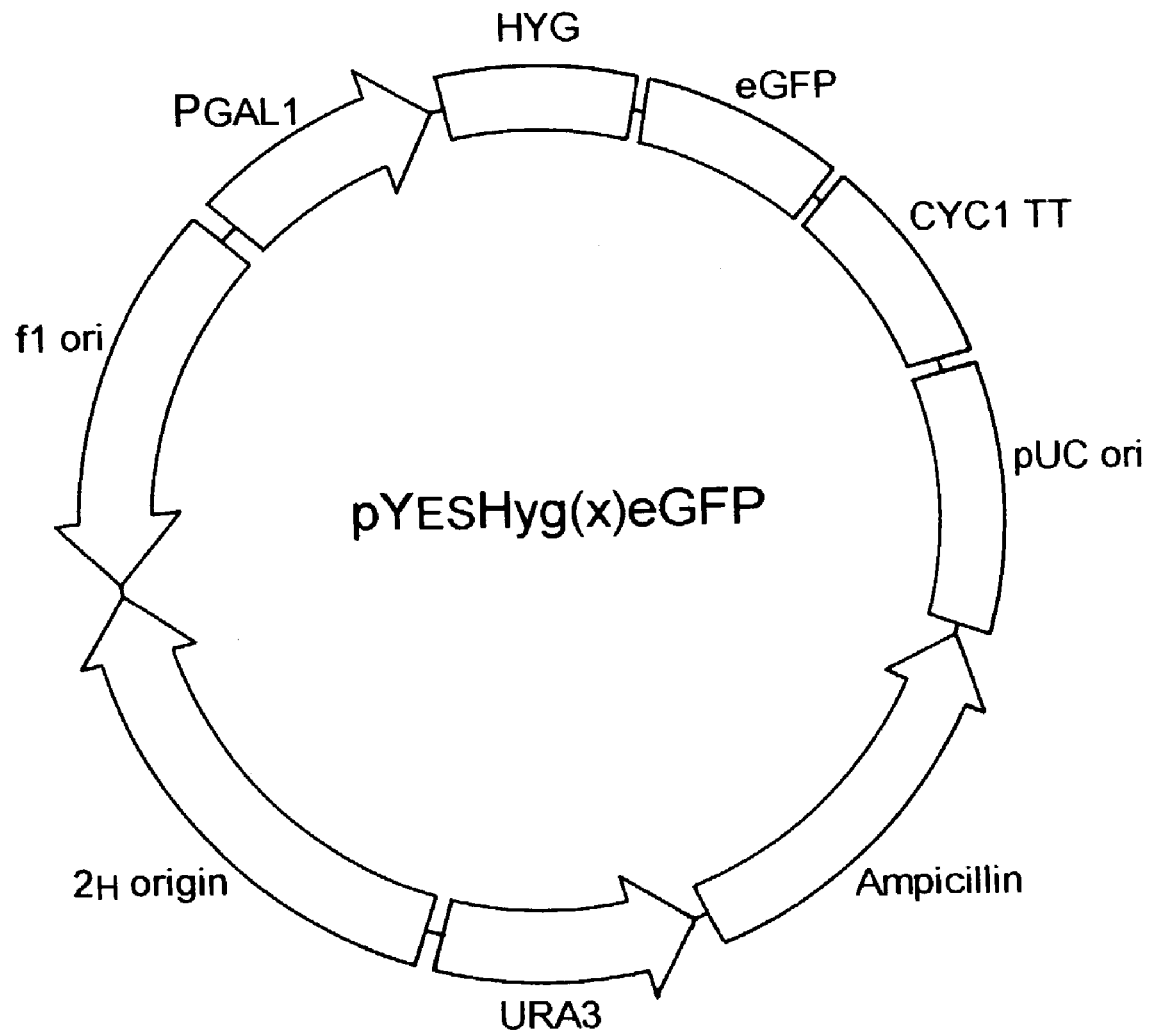
FIG. 6. pYESHyg(x)eGFP plasmid. This plasmid is a construct similar to the pAURHyg(x)eGFP construct shown in FIG. 7, except the promoter is the inducible GAL1 promoter. This promoter is inducible with galactose, leaky in the presence of raffinose, and repressed in the presence of dextrose.
Figure 7:
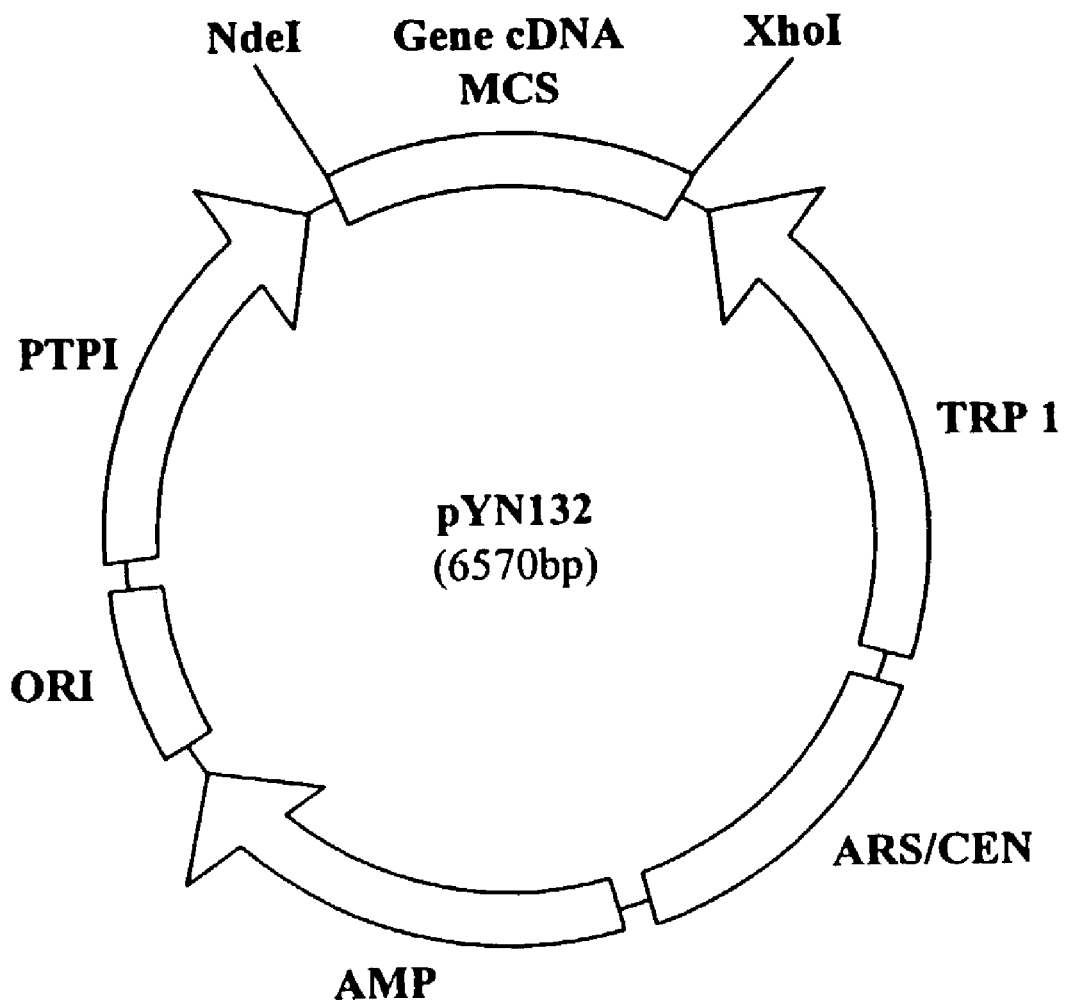
FIG. 7. pYN132 plasmid. This figure shows the plasmid structure including the constitutive promoter from the TPL1 gene, which directs expression of the cDNA cloned downstream.

Nucleic acid sequence alteration in yeast strains expressing DNA repair gene(s) from plasmids. We test the effect on nucleic acid sequence alteration efficiency of increasing expression of DNA repair genes, including genes in the RAD52 epistasis group, mismatch repair genes and nucleotide excision repair genes. We test the effect of expression of these genes both individually and in groups of two or more. We employ plasmids with inducible promoters, for example, the plasmid described in FIG. 6, directing expression of DNA repair genes. Alternatively, we use plasmids with constitutive promoters to direct expression of DNA repair genes, for example, the plasmids described in FIGS. 1, 2 and 4.

We test the ability of oligonucleotides shown in FIG. 3 to alter a nucleic acid sequence in vivo using yeast strains with additional copies of gene(s) of the RAD52 epistasis group, the mismatch repair group or the nucleotide excision repair group. In these experiments we use derivatives of LSY678 wild type containing the plasmid pYN132 or the derivatives of pYN132 comprising a cloned copy of a gene from the RAD52 epistasis group, the mismatch repair group or the nucleotide excision repair group. These strains also contain one of the plasmids pAURHYG(rep)eGFP, pAURHYG(ins) eGFP or pAURHYG(del)eGFP as a reporter for monitoring nucleic acid sequence alteration. Alternatively, these strains comprise the one or more copies of the integrational plasmid pAUR101-HYG(x)eGFP as a reporter for monitoring nucleic acid sequence alteration. We confirm expression of the cloned DNA repair gene in these strains by northern blot and/or western blot analysis. Alternatively, we confirm expression by monitoring complementation of methyl methanesulfonate (MMS) sensitivity in, e.g., a RAD51, RAD52 or RAD54 mutant by a plasmid overexpressing the corresponding gene.

We introduce, for example, plasmids expressing RAD10, RAD51, RAD52, RAD54, RAD55, MRE11, PMS1, REC2 or XRS2 into LSY678 (wild type) and monitor the ability of the single-stranded oligonucleotide vector, Hyg3S/74NT, to direct nucleic acid sequence alteration in the pAURHYG(x) eGFP plasmid. As shown in Table 9, Table 12 and Tables 17–18, results from these experiments indicate that additional expression of any one of the RAD10, RAD51, RAD52, RAD54, MRE11, PMS1 or XRS2 genes results in an increase in nucleic acid sequence alteration efficiency ranging from 1.2-fold (RAD10) to 7.5-fold (RAD51). These data clearly indicate that additional copies of particular DNA repair proteins results in increased nucleic acid sequence alteration efficiency. We also introduce plasmids expressing multiple proteins into LSY678 (wild type) and monitor the efficiency of nucleic acid sequence alteration as shown in Table 10 and Table 19. We also test other genes from the RAD52 epistasis group, the mismatch repair group or the nucleotide excision repair group for enhancement of nucleic acid sequence alteration efficiency.

We test nucleic acid sequence alteration efficiency as described above using yeast strains further comprising mutation(s) in the RAD52 epistasis group, the mismatch repair group or the nucleotide excision repair group. For example, we introduce pYN132-derived plasmids expressing RAD10, RAD51, RAD52, RAD54, RAD55, MRE11, PMS1, REC2 or XRS2 into LSY678 strains with mutations in RAD51, RAD52, RAD 54, MRE11 or PMS1. We then monitor the ability of the single-stranded oligonucleotide vector, Hyg3S/74NT, to direct nucleic acid sequence alteration in the pAURHYG(x)eGFP plasmid. As shown in Table 11, Table 13, Table 15, and Tables 17–18, we observe that strains with mutations in RAD51, RAD52, RAD54, MRE11 or PMS1 containing pYN132 exhibit reduced alteration efficiency relative to the wild type containing pYN132 shown in Table 9. These data are consistent with results from mutant strains shown in Table 6. In general, we observe that expressing RAD10, RAD51, RAD54, MRE11 or PMS1 in these yeast strains results in increased nucleic acid sequence alteration efficiency relative to the mutant with the empty pYN132 vector. These data indicate that additional expression of these genes results in enhancement of alteration efficiency in the mutants as it does in the wild type. We observe that a RAD52 mutant expressing RAD51 from a plasmid gives very high alteration efficiency. We observe that a PMS1 mutant expressing RAD51 from a plasmid gives the highest alteration efficiency of any strain tested. We also test the effect of expressing multiple proteins in mutant yeast stains and monitor the efficiency of nucleic acid sequence alteration.

We also monitor nucleic acid sequence alteration efficiency on chromosomal targets in yeast strains with additional copies of gene(s) of the RAD52 epistasis group, the mismatch repair group or the nucleotide excision group. For example, we introduce pYN132-derived plasmids expressing RAD51, RAD52, RAD54, RAD51+RAD54, RAD51+ RAD52, MRE11, XRS2 or MRE11+XRS2 into yeast strains containing integrated copies of the pAUR101-HYG(x)eGFP plasmids. The results from an experiment using a strain with integrated pAUR101-HYG(rep)eGFP are shown in Table 19. These results are consistent with results observed with episomal target experiments.

We also determine nucleic acid sequence alteration efficiency on chromosomal target sequences as described above using yeast strains comprising mutation(s) in the RAD52 epistasis group, the mismatch repair group or the nucleotide excision repair group. For example, we introduce pYN132-derived plasmid(s) expressing RAD51, RAD52, RAD54, MRE11, PMS1, REC2 or XRS2 into LSY678 strains with an integrated copy of pAUR101-HYG(x)eGFP and mutation(s) in one or more of the RAD51, RAD52, MRE11 and PMS1 genes. We then monitor the ability of the single-stranded oligonucleotide vector, Hyg3S/74NT, to direct nucleic acid sequence alteration in the integrated pAUR101-HYG(x) eGFP plasmid. Results of one such experiment are shown in Table 16.

We also test the effect of heterologous expression of DNA repair genes from other organisms, including, for example, other fungi, animals, plants and bacteria.

We also use additional oligonucleotides to assay the ability of individual oligonucleotides to correct multiple mutations in the pAURHYG(x)eGFP plasmid contained in yeast strains with altered expression or activity of gene(s) in the RAD52 epistasis group, the mismatch repair group and/or the nucleotide excision repair group. These include, for example, one that alters two basepairs that are 3 nucleotides apart is a 74-mer with the sequence 5'-CTCGT-GCTTTCAGCTTCGATGTAGGAGGGCGTGGGTACGTCCTGCGGGTAAATAGCTGCGCCGATGGTTTC TAC-3' (SEQ ID NO: 17); a 74-mer that alters two basepairs that are 15 nucleotides apart with the sequence 5'-CTCGT-GCTTTCAGCTTCGATGTAGGAGGGCGTGGATACGTCCTGCGGGTAAACAGCTGCGCCGATGGTTTCTAC-3' (SEQ ID NO: 18); and a 74-mer that alters two basepairs that are 27 nucleotides apart with the sequence 5'-CTCGTGCTTTCAGCTTCGAT-GTAGGAGGGCGTGGATACGTCCTGCGGGTAAATAGCTGCGCCGACGGTTTCTAC (SEQ ID NO: 19). The nucleotides in these oligonucleotides that direct alteration of the target sequence are underlined and in boldface. These oligonucleotides are modified in the same ways as the previously described oligonucleotides.

We also test the ability of oligonucleotides shown in FIG. 1 to alter a nucleic acid sequence in vivo using yeast strains containing the plasmid pAURNeo(x)FlAsH (FIG. 4) and which also have altered expression or activity of gene(s) in the RAD52 epistasis group, the mismatch repair group and/or the nucleotide excision repair group. This plasmid is constructed by inserting a synthetic expression cassette containing a neomycin phosphotransferase (kanamycin resistance) gene and an extended reading frame that encodes a receptor for the FlAsH ligand into the pAUR123 shuttle vector (Panvera Corp., Madison, Wis.). We make constructs with the same mutation as in pK$^s$m4021. The resulting construct replicates in S. cerevisiae at low copy number, confers resistance to aureobasidinA and constitutively expresses the Neo(x)FlAsH fusion product from the ADH1 promoter. By extending the reading frame of this gene to code for a unique peptide sequence capable of binding a small ligand to form a fluorescent complex, restoration of expression by alteration of the stop codon can be detected in real time using confocal microscopy. Upon alteration of the truncated Neo(−)FlAsH product to generate the Neo(+) FlAsH fusion product the translated fusion protein binds a ligand (FlAsH-EDT2) imparting a green fluorescence onto the cells. Additional constructs using any target gene fused to the FlAsH peptide may be made using this model system to test additional nucleic acid sequence alteration events.

To detect the presence of the Neo(+)FlAsH fusion product in yeast cells, we prepare loading buffer by mixing FlAsH ligand into YPD containing 1M sorbitol and 20 μM Disperse 3. The ligand molecules are mixed into the YPD at 1 μM FlAsH EDT2 and 10 μM 1,2 ethanedithiol (EDT) (Sigma). We then mix 100 μl of cells with an equal volume of wash buffer comprising HBS, 1 mM sodium pyruvate, 10 μM EDT, 1 M sorbitol and 20 μM Disperse 3. We then image the cells with a Zeiss LSM510 laser scanning microscope on a Zeiss Axiovert 100 m using the 488/568 nm excitation line of an Omnichrome Ar—Kr laser with appropriate emission filters (505–550 nm bandpass for FlAsH-EDT2 binding). We simultaneously acquire laser scanning transmitted or differential interference contrast images with all fluorescent images using 488 nm excitatory. We load samples into a Lab-Tek II chambered #1.5 Coverglass system (Nalge Nunc International, IL) and image them using a Zeiss 63×C-Apochromet water immersion lens (NA 1.2). All samples, including positive and negative controls, are integrated under identical conditions (laser power, pinhole, PMT gap offset, etc.) for a given set of experiments.

We observe alteration of a mutation in the neomycin phosphotransferase gene (Neo) harbored in yeast strain LSY678 using a FlAsH-EDT2 model system. We electroporate KanGG or another oligonucleotide directing nucleic acid sequence alteration into either LSY386 or LSY678 containing stable copies of the pAURNeo(−)FlAsH plasmid. We measure uptake of oligonucleotide using Texas Red conjugated oligonucleotide and optimize electroporation conditions so that over 80% of the surviving cells receive the oligonucleotide. Alternatively, we measure uptake using $^{32}$P-labeled oligonucleotides. We grow the strains at 30° C. to a density of about $10^7$ cells/ml in 40 ml of YPD medium, wash them twice with 25 ml sterile water and once with 1 ml of 1M sorbitol, and resuspend in 120 μl 1M sorbitol. We electroporate 40 μl (about $10^8$) cells with oligonucleotide, allow the cells to recover in 1 ml of YPD for 30 minutes, and then wash the cells twice with 1M sorbitol before detecting the radioactivity remaining. We use these measurement methods to compare uptake between different strains and we observe that uptake is generally about the same (less than a two-fold difference; Table 20).

Figure 5:
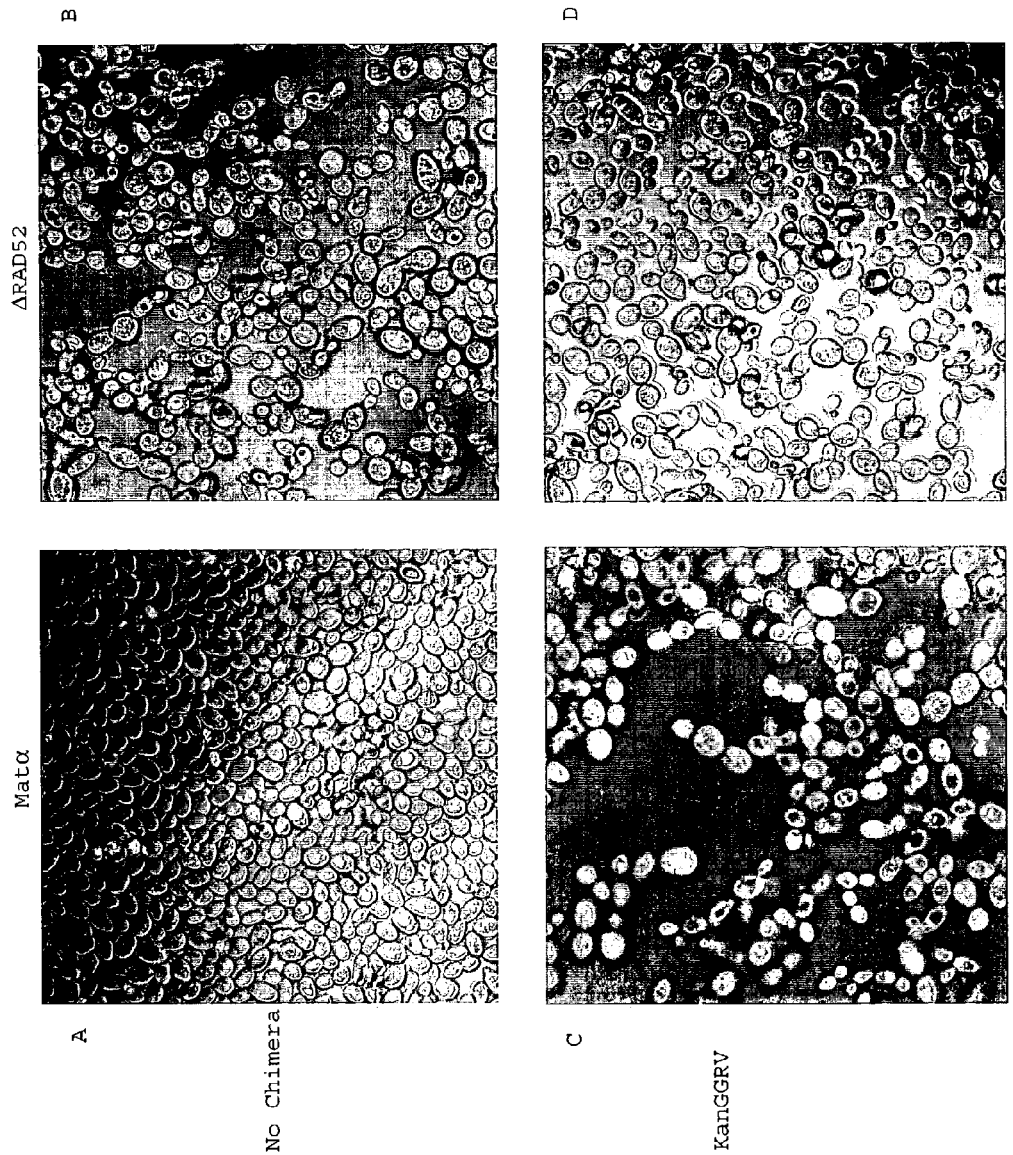
FIG. 5. Fluorescent microscopy figures of targeting in the FlAsH system. This figure shows confocal microscopy of yeast strains before and after transfection by DNA/RNA CO kanGGrv. Converted yeast cells are indicated by bright green fluorescence. (A) Upper left: wild type, nontargeted. Upper right: Δrad52, nontargeted. (C) Lower left: wild type, targeted. (D) Lower right: Δrad52, targeted.

In the absence of KanGG, or another oligonucleotide directing nucleic acid sequence alteration, we observe only a low level of auto-fluorescence after addition of FlAsH-EDT2 in both LSY678 (FIG. 5A) and LSY386 (FIG. 5B) by confocal microscopy. However, when we introduce KanGG into the cells, we observe many corrected cells in both LSY678 and LSY378 as seen in FIG. 5C and FIG. 5D, respectively. We see a significant increase in the number of cells exhibiting green fluorescence in the LSY378 strain lacking RAD52 (FIG. 5D) relative to the LSY678 strain (FIG. 5C). This result reflects a higher degree of gene repair in the strain lacking RAD52 gene function. Alteration of pAURNeo(−)FlAsH also confers resistance to G418 selection in yeast cells. Therefore we grow representative samples exhibiting green fluorescence on agar plates containing G418. We then determine the DNA sequence of the plasmid in these cells. The sequence analysis illustrates that the targeted base is changed from a G to a C as designed in plasmids isolated after G418 selection. We perform similar experiments in yeast strains with altered levels of expression or activity of other proteins in the RAD52 epistasis group, the mismatch repair group and the nucleotide excision repair group.

Oligonucleotides targeting the sense strand direct nucleic acid sequence alteration more efficiently in yeast mutants. We compare the ability of single-stranded oligonucleotides to target each of the two strands of the target sequence of pAURHYG(ins)eGFP, pAURHYG(rep)eGFP or pAURHYG(Δ)eGFP present in LSY678 mutant strains with increased or decreased expression of DNA repair genes. For example, the results of an experiment performed with yeast strains having mutations in RAD1 and RAD10 are presented in Table 8. The data from this experiment indicate that an oligonucleotide, HygE3T/74NT, with sequence complementary to the sense strand (i.e. the strand of the target sequence that is identical to the mRNA) of the target sequence facilitates nucleic acid sequence alteration approximately ten-fold more efficiently than an oligonucleotide, HygE3T/74, with sequence complementary to the non-transcribed strand which serves as the template for the synthesis of RNA. However, regardless of the reduced efficiency observed in yeast strains with mutations in DNA repair genes, the oligonucleotides are clearly still able to target either strand of the target sequence. In addition, the role of transcription of the target gene is investigated using plasmids with inducible promoters such as that described in FIG. 6.

Influence of DNA repair genes in other cells. In addition to testing the effect of DNA repair genes in the above-described yeast assay system, we test the effect of altering the expression or the activity of DNA repair genes in other cells, including, for example, other fungi, animal, plant and bacterial cells. We use other cells with normal DNA repair genes as well as cells that have altered levels or activity of DNA repair genes, including, for example, human and bacterial cells with mutations in the homologous genes or expressing additional copies of the homologous genes. For example, we use cells that are transiently or stably transformed with vectors that express either native or heterologous DNA repair genes. To monitor nucleic acid sequence alteration in these cells, we employ a reporter-gene assay system, for example, kanamycin resistance, hygromycin resistance or GFP expression. Alternatively, we assay the ability of an oligonucleotide to direct nucleic acid sequence alteration of a target present in the genome of the target cell, for example, we monitor conversion of the sickle T ($β^S$) mutation in the β-globin gene to the normal A ($β^A$) allele or vice-versa.

Tables are attached hereto.

TABLE 4

Nucleic acid sequence alteration of different mutations in wild-type *Saccharomyces cerevisiae*

| Amount of Oligonucleotide | Correcting Oligonucleotide Tested | | |
|---|---|---|---|
| (μg) | HygE3T/74 | HygE3T/74NT | Fold |
| Repair of pAURHYG(rep)eGFP | | | |
| 0 | 0* | 0 | 0× |
| 1.0 | 5 (0.03) | 238 (1.47) | 47.6× |
| 2.5 | 99 (0.61) | 704 (4.37) | 7.1× |
| 5.0 | 204 (1.26) | 1,406 (8.73) | 6.8× |
| 7.5 | 69 (0.42) | 998 (6.20) | 14.5× |
| 10.0 | 19 (0.12) | 261 (1.62) | 13.7× |

TABLE 4-continued

Nucleic acid sequence alteration of different mutations in wild-type *Saccharomyces cerevisiae*

| Amount of Oligonucleotide (μg) | Correcting Oligonucleotide Tested | | |
|---|---|---|---|
| | HygE3T/74 | HygE3T/74NT | Fold |
| Repair of pAURHYG(Δ)eGFP | | | |
| 0 | 0 | 0 | 0× |
| 1.0 | 1 (0.01) | 1 (0.01) | 1.0× |
| 2.5 | 18 (0.11) | 68 (0.42) | 3.8× |
| 5.0 | 70 (0.43) | 308 (1.91) | 4.4× |
| 7.5 | 47 (0.29) | 276 (1.71) | 5.9× |
| 10.0 | 11 (0.07) | 137 (0.85) | 12.5× |
| Repair of pAURHYG(ins)eGFP | | | |
| 0 | 0 | 0 | 0× |
| 1.0 | 5 (0.03) | 45 (0.28) | 9.0× |
| 2.5 | 47 (0.29) | 387 (2.4) | 8.2× |
| 5.0 | 199 (1.24) | 623 (3.87) | 3.1× |
| 7.5 | 54 (0.34) | 398 (2.47) | 7.4× |
| 10.0 | 17 (1.10) | 271 (1.68) | 15.9× |

*Average colony count on hygromycin plates from four experiments is shown. Numbers in parentheses indicate the number of hygromycin-resistant colonies per aureobasidin-resistant colony.

TABLE 5

Nucleic acid sequence alteration directing alteration of the mutation in pAURHYG(rep)eGFP

| Yeast Strain* | Colonies on Hygromycin | Colonies on Aureobasidin (/10⁵) | Alteration Efficiency | Fold |
|---|---|---|---|---|
| wild type | 1,218 | 286 | 4.26 | 1× |
| RAD52 Epistasis Group Mutants | | | | |
| rad51 | 104 | 168 | 0.62 | 0.14× |
| rad52 | 266 | 81 | 3.29 | 0.77× |
| rad51/52 | 212 | 39 | 5.45 | 1.28× |
| rad54 | 2 | 103 | 0.02 | 0× |
| rad55 | 0 | 1,230 | 0 | 0× |
| rad57 | 984 | 57 | 17.26 | 4.05× |
| rad59 | 1,198 | 392 | 3.06 | 0.71× |
| mre11 | 12 | 18 | 0.63 | 0.15× |
| rad50 | 336 | 58 | 2.09 | 0.49× |
| xrs2 | 29 | 44 | 0.66 | 0.15× |
| Mismatch Repair Group Mutants | | | | |
| msh2 | 0 | 976 | 0 | 0× |
| msh3 | 0 | 1,035 | 0 | 0× |
| msh6 | 1,270 | 541 | 2.35 | 0.55× |
| pms1 | 2,280 | 20 | 114 | 26.76× |
| Nucleotide Excision Repair Mutants | | | | |
| rad1 | 1,380 | 391 | 8.52 | 2.00× |
| rad10 | 54 | 361 | 0.15 | 0.04× |
| rad2 | 919 | 243 | 3.78 | 0.89× |
| rad23 | 66 | 151 | 0.44 | 0.10× |
| exo1 | 486 | 124 | 3.92 | 0.92× |

*Each strain is wild type except for the indicated mutation(s). The mutations used in these experiments are generally knockout mutations.

TABLE 6

Nucleic acid sequence alteration directing alteration of the mutation in pAURHYG(ins)eGFP

| Yeast Strain* | Colonies on Hygromycin | Colonies on Aureobasidin (10⁵) | Alteration Efficiency | Fold |
|---|---|---|---|---|
| wild type | 256 | 74 | 3.46 | 1× |
| RAD52 Epistasis Group Mutants | | | | |
| rad51 | 19 | 32 | 0.59 | 0.17× |
| rad52 | 31 | 36 | 0.86 | 0.24× |
| rad51/52 | 3 | 86 | 0.3 | 0.01× |
| rad54 | 0 | 170 | 0 | 0× |
| rad55 | 0 | 32 | 0 | 0× |
| rad57 | 34 | 103 | 0.33 | 0.10× |
| rad59 | 116 | 47 | 2.47 | 0.71× |
| mre11 | 3 | 34 | 0.09 | 0.03× |
| rad50 | 1 | 17 | 0.06 | 0.02× |
| xrs2 | 6 | 168 | 0.04 | 0.01× |
| Mismatch Repair Group Mutants | | | | |
| msh2 | 0 | 51 | 0 | 0× |
| msh3 | 1 | 18 | 0.05 | 0.02× |
| msh6 | 0 | 49 | 0 | 0× |
| pms1 | 111 | 6 | 18.5 | 5.35× |
| Nucleotide Excision Repair Mutants | | | | |
| rad1 | 52 | 88 | 0.59 | 0.17× |
| rad10 | 14 | 101 | 0.14 | 0.04× |
| rad2 | 113 | 63 | 1.79 | 0.52× |
| rad23 | 1 | 144 | 0.01 | 0× |
| exo1 | 2 | 197 | 0.01 | 0× |

*Each strain is wild type except for the indicated mutation(s). The mutations used in these experiments are generally knockout mutations.

TABLE 7

Nucleic acid sequence alteration directing alteration of the mutation in pAURHYG(Δ)eGFP

| Yeast Strain* | Fold Change in Alteration Efficiency |
|---|---|
| wild type | 1× |
| RAD52 Epistasis Group Mutants | |
| rad51 | 0.47× |
| rad52 | 0.05× |
| rad51/52 | 0.13× |
| mre11 | 1.10× |
| Mismatch Repair Group Mutants | |
| msh2 | 0× |
| msh3 | 0.02× |
| msh6 | 0× |
| Nucleotide Excision Repair Mutants | |
| rad1 | 0× |
| rad10 | 0.04× |

*Each strain is wild type except for the indicated mutation(s). The mutations used in these experiments are generally knockout mutations.

TABLE 8

Alteration with an oligonucleotide targeting the sense strand is more efficient

| | Colonies on Hygromycin | | |
|---|---|---|---|
| Yeast Strain | Kan70T | HygE3T/74 | HygE3T/74NT |
| rad1 | 0 | 3 | 53(15×)* |
| rad10 | 0 | 2 | 14(6×)* |

*The numbers in parentheses represent the fold increase in efficiency for targeting the non-transcribed strand as compared to the other strand of a DNA duplex that encodes a protein.
**Each strain is wild type except for the indicated mutation(s). The mutations used in these experiments are generally knockout mutations.

TABLE 9

Nucleic acid sequence alteration in yeast strains with increased levels of DNA repair proteins

| Yeast Strain* | Hyg3S/ 74NT (μg) | Hyg$^r$ | Aur$^r$ ($10^4$) | Alteration efficiency ($1/10^5$) | Fold |
|---|---|---|---|---|---|
| wild type/pYN132 | 0 | 0 | 931 | 0 | N/A |
| wild type/pYN132 | 5 | 249 | 801 | 3.1 | 1 |
| wild type/pYNRAD51 | 5 | 2,700 | 1,152 | 23.4 | 7.5 |
| wild type/pYNRAD52 | 5 | 1,512 | 748 | 20.3 | 6.5 |
| wild type/pYNRAD55 | 5 | 283 | 1,016 | 2.8 | 0.9 |
| wild type/pYNMRE11 | 5 | 920 | 728 | 12.6 | 4.1 |
| wild type/pYNPMS1 | 5 | 406 | 804 | 5.0 | 1.6 |

TABLE 10

Nucleic acid sequence alteration in yeast strains with increased levels of multiple DNA repair proteins

| Yeast Strain* | Hyg3S/ 74NT (μg) | Hyg$^r$ | Aur$^r$ ($10^4$) | Alteration efficiency ($1/10^5$) | Fold |
|---|---|---|---|---|---|
| wild type/pYN132 | 5 | 330 | 141 | 23.4 | 1 |
| wild type/pYNRAD51 | 5 | 1,360 | 109 | 124.77 | 5.33× |
| wild type/pYNRAD54 | 5 | 886 | 70 | 126.57 | 5.41× |
| wild type/pYNMRE11 | 5 | 456 | 74 | 61.62 | 2.63× |
| wild type/pYNRAD51 + pYNRAD54 | 5 | 978 | 78 | 125.38 | 5.36× |
| wild type/pYNRAD51 + pYNMRE11 | 5 | 236 | 69 | 34.2 | 1.46× |
| wild type/pYNRAD54 + pYNMRE11 | 5 | 412 | 159 | 25.91 | 1.11× |
| wild type/pYNRAD51 + pYNRAD54 + pYNMRE11 | 5 | 1,120 | 71 | 157.75 | 6.74× |

*All strains also contain pAURHyg(ins)eGFP as the target for alteration. All yeast strains are wild type for all DNA repair proteins and contain plasmids expressing DNA repair proteins as indicated.

TABLE 11

Nucleic acid sequence alteration in yeast strains with increased levels of DNA repair proteins

| Yeast Strain* | Hyg3S/ 74NT (μg) | Hyg$^r$ | Aur$^r$ ($10^4$) | Alteration efficiency ($1/10^5$) | Fold |
|---|---|---|---|---|---|
| rad51/pYN132 | 0 | 0 | 1,012 | 0 | N/A |
| rad51/pYN132 | 5 | 18 | 708 | 0.25 | 1 |
| rad51/pYNRAD51 | 5 | 159 | 1,392 | 1.14 | 4.6 |
| rad51/pYNRAD52 | 5 | 39 | 1,586 | 0.24 | 1 |
| rad51/pYNRAD55 | 5 | 26 | 1,372 | 0.19 | 0.8 |
| rad51/pYNMRE11 | 5 | 8 | 426 | 0.18 | 0.7 |
| rad51/pYNPMS1 | 5 | 33 | 984 | 0.33 | 1.3 |
| rad52/pYN132 | 0 | 0 | 518 | 0 | N/A |
| rad52/pYN132 | 5 | 140 | 644 | 2.17 | 1 |
| rad52/pYNRAD51 | 5 | 3,532 | 832 | 42.4 | 19.3 |
| rad52/pYNRAD52 | 5 | 195 | 684 | 2.85 | 1.3 |
| rad52/pYNRAD55 | 5 | 69 | 308 | 2.24 | 1.0 |
| rad52/pYNMRE11 | 5 | 63 | 122 | 5.16 | 2.4 |
| rad52/pYNPMS1 | 5 | 67 | 145 | 4.62 | 2.1 |
| mre11/pYN132 | 0 | 0 | 302 | 0 | N/A |
| mre11/pYN132 | 5 | 2 | 260 | 0.077 | 1 |
| mre11/pYNRAD51 | 5 | 1 | 235 | 0.042 | 0.6 |
| mre11/pYNRAD52 | 5 | 3 | 135 | 0.022 | 2.8 |
| mre11/pYNRAD55 | 5 | 20 | 217 | 0.922 | 11.9 |
| mre11/pYNMRE11 | 5 | 57 | 588 | 0.969 | 12.6 |
| mre11/pYNPMS1 | 5 | 1 | 147 | 0.067 | 0.9 |

*All strains also contain pAURHyg(ins)eGFP as the target for alteration. All yeast strains are wild type except for a single mutation in the indicated DNA repair protein and contain plasmids expressing wildtype DNA repair proteins as indicated. The mutations used in these experiments are generally knockout mutations.

TABLE 12

Nucleic acid sequence alteration in yeast strains with increased levels of DNA repair proteins

| Yeast Strain* | Hyg3S/ 74NT (μg) | Hyg$^r$ | Aur$^r$ ($10^4$) | Alteration efficiency ($1/10^5$) | Fold |
|---|---|---|---|---|---|
| wild type/pYN132 | 0 | 0 | 931 | 0 | N/A |
| wild type/pYN132 | 5 | 827 | 740 | 11.17 | 1 |
| wild type/pYNRAD10 | 5 | 1,112 | 812 | 13.69 | 1.2 |
| wild type/pYNRAD54 | 5 | 4,320 | 970 | 44.54 | 4.0 |
| wild type/pYNREC2 | 5 | 152 | 686 | 2.22 | 0.20 |
| wild type/pYNXRS2 | 5 | 937 | 670 | 13.98 | 1.25 |
| wild type/pYNPRAD51 + RAD52 | 5 | 1,042 | 908 | 11.48 | 1.02 |

*All strains also contain pAURHyg(ins)eGFP as the target for alteration. All yeast strains are wild type for all DNA repair proteins and contain plasmids expressing DNA repair proteins as indicated

TABLE 13

Nucleic acid sequence alteration in yeast strains with increased levels of DNA repair proteins

| Yeast Strain* | Hyg3S/ 74NT (μg) | Hyg$^r$ | Aur$^r$ ($10^4$) | Alteration efficiency ($1/10^5$) | Fold |
|---|---|---|---|---|---|
| Δrad51/pYN132 | 0 | 0 | 1,012 | 0 | N/A |
| Δrad51/pYN132 | 5 | 50 | 576 | 0.87 | 1 |
| Δrad51/pYNRAD10 | 5 | 21 | 548 | 0.38 | 0.44 |
| Δrad51/pYNRAD54 | 5 | 10 | 683 | 0.15 | 0.17 |
| Δrad51/pYNREC2 | 5 | 28 | 456 | 0.61 | 0.77 |
| Δrad51/pYNXRS2 | 5 | 15 | 890 | 0.17 | 0.19 |
| Δrad52/pYN132 | 0 | 0 | 518 | 0 | N/A |
| Δrad52/pYN132 | 5 | 57 | 700 | 0.81 | 1 |
| Δrad52/pYNRAD10 | 5 | 97 | 777 | 1.25 | 1.54 |
| Δrad52/pYNRAD54 | 5 | 388 | 792 | 4.89 | 6.04 |
| Δrad52/pYNREC2 | 5 | 12 | 678 | 0.18 | 0.22 |
| Δrad52/pYNXRS2 | 5 | 56 | 609 | 0.92 | 1.06 |
| wild type/pYN132 | 5 | 465 | 129 | 3.6 | 1 |
| Δmre11/pYN132 | 0 | 0 | 302 | 0 | N/A |
| Δmre11/pYN132 | 5 | | | | |
| Δmre11/pYNRAD10 | 5 | 184 | 41 | 4.49 | 1.25 |
| Δmre11/pYNRAD54 | 5 | 12 | 17 | 0.71 | 0.20 |
| Δmre11/pYNREC2 | 5 | 83 | 30 | 2.77 | 0.77 |
| Δmre11/pYNXRS2 | 5 | 9 | 14 | 0.64 | 0.18 |

*All strains also contain pAURHyg(ins)eGFP as the target for alteration. All yeast strains are wild type except for a single mutation in the indicated DNA repair protein and contain plasmids expressing wildtype DNA repair proteins as indicated. The mutations used in these experiments are generally knockout mutations.

TABLE 14

Gene repair of chromosomal mutations in wild-type Saccharomyces cerevisiae

| Amount of Oligonucleotide (μg) | Correcting Oligonucleotide Tested | | Fold Difference in Alteration Efficiency |
|---|---|---|---|
| | HygE3T/74 | HygE3T/74NT | |
| Repair of integrated pAUR101-HYG(rep)GFP | | | |
| 0 | 0* | 0 | 0× |
| 2.5 | 652 (140) | 3,108 (180) | 3.7× |
| 5.0 | 1,060 (120) | 4,203 (139) | 3.4× |
| 7.5 | 2,052 (112) | 6,120 (116) | 2.8× |
| 10.0 | 2,012 (121) | 3,932 (155) | 1.5× |

*Average colony count on hygromycin plates from three experiments is shown. Numbers in parentheses indicate the number of aureobasidin-resistant colonies (/$10^5$).

TABLE 15

Nucleic acid sequence alteration in yeast strains with increased levels of DNA repair proteins

| Yeast Strain* | Hyg3S/ 74NT (μg) | Hyg$^r$ | Aur$^r$ ($10^4$) | Alteration efficiency ($1/10^5$) | Fold |
|---|---|---|---|---|---|
| Δpms1/pYN132 | 5 | 11 | 120 | 9.17 | 1× |
| Δpms1/pYNRAD51 | 5 | 11,890 | 578 | 2057 | 224× |
| Δpms1/pYNRAD52 | 5 | 53 | 241 | 22 | 2.4× |
| Δpms1/pYNRAD54 | 5 | 252 | 740 | 34 | 3.7× |
| Δpms1/pYNRAD55 | 5 | 255 | 593 | 43 | 4.7× |
| Δpms1/pYNMRE11 | 5 | 126 | 247 | 51 | 5.6× |
| Δpms1/pYNPMS1 | 5 | 64 | 256 | 25 | 2.7× |
| Δpms1/pYNXRS2 | 5 | 141 | 359 | 39 | 4.3× |
| Δpms1/pYNRAD10 | 5 | 17 | 809 | 2.1 | 0.23× |
| Δpms1/pYNRAD51 + pYNRAD54 | 5 | 641 | 774 | 83 | 9.1× |

*All strains also contain pAURHyg(rep)eGFP as the target for alteration. All yeast strains are wild type except for a single mutation in the indicated DNA repair protein and contain plasmids expressing wild-type DNA repair proteins as indicated. The mutations used in these experiments are generally knockout mutations.

TABLE 16

Nucleic acid sequence alteration in yeast strains with increased levels of DNA repair proteins

| Yeast Strain* | Hyg3S/ 74NT (μg) | Alteration efficiency (1/10$^5$) | Fold |
|---|---|---|---|
| Δpms1/pYN132 | 5 | 0.06 | 1× |
| Δpms1/pYNRAD51 | 5 | 7.74 | 129× |
| Δpms1/pYNRAD52 | 5 | 0.92 | 15.3× |
| Δpms1/pYNRAD54 | 5 | 51.65 | 861× |
| Δpms1/pYNRAD55 | 5 | 9.94 | 166× |
| Δpms1/pYNMRE11 | 5 | 0.16 | 2.7× |
| Δpms1/pYNPMS1 | 5 | 0.24 | 4.0× |

*All strains contain an integrated pAUR101-HYG(rep)eGFP as the target for alteration. All yeast strains are wild type except for a single mutation in the indicated DNA repair protein and contain plasmids expressing wild-type DNA repair proteins as indicated. The mutations used in these experiments are generally knockout mutations.

TABLE 17

Nucleic acid sequence alteration in yeast strains with increased levels of DNA repair proteins

| Yeast Strain* | Hyg3S/ 74NT (μg) | Hyg$^r$ (mean ± SD) | Alteration efficiency (1/10$^5$) | Fold |
|---|---|---|---|---|
| LSY678(wt)/pYN132 | 5 | 2632.25 ± 389.48 | 12.64 ± 3.66 | 1× |
| LSY678(wt)/pYNRAD51 | 5 | 5008.33 ± 401.44 | 49.41 ± 13.68 | 3.9× |
| LSY678(wt)/pYNRAD52 | 5 | 276.13 ± 49.78 | 1.52 ± 0.31 | 0.12× |
| LSY678(wt)/pYNRAD54 | 5 | 4156.57 ± 897.58 | 34.76 ± 5.56 | 2.75× |
| Δrad51/pYN132 | 5 | 232.56 ± 42.11 | 1.01 ± 0.21 | 0.080× |
| Δrad51/pYNRAD51 | 5 | 7189.32 ± 688.74 | 45.91 ± 12.37 | 3.6× |
| Δrad51/pYNRAD52 | 5 | 202.14 ± 30.31 | 0.94 ± 0.35 | 0.074× |
| Δrad51/pYNRAD54 | 5 | 507.41 ± 96.34 | 1.70 ± 0.27 | 0.13× |
| Δrad52/pYN132 | 5 | 2315.14 ± 578.75 | 17.63 ± 7.95 | 1.4× |
| Δrad52/pYNRAD51 | 5 | 12400.57 ± 1356.16 | 299.51 ± 41.76 | 24× |
| Δrad52/pYNRAD52 | 5 | 908.51 ± 127.12 | 8.28 ± 1.32 | 0.66× |
| Δrad52/pYNRAD54 | 5 | 9180.32 ± 1774.58 | 201.97 ± 33.15 | 16× |
| Δrad54/pYN132 | 5 | 614.79 ± 79.92 | 3.29 ± 0.53 | 0.26× |
| Δrad54/pYNRAD51 | 5 | 1224.27 ± 125.88 | 6.58 ± 0.92 | 0.52× |
| Δrad54/pYNRAD52 | 5 | 291.40 ± 67.02 | 1.64 ± 0.26 | 0.13× |
| Δrad54/pYNRAD54 | 5 | 1846.51 ± 430.68 | 10.86 ± 2.28 | 0.86× |

*All strains also contain pAURHyg(rep)eGFP as the target for alteration. All yeast strains are wild type except for a single mutation in the indicated DNA repair protein and contain plasmids expressing wild-type DNA repair proteins as indicated. The mutations used in these experiments are generally knockout mutations. The results shown are the averages from five experiments.

TABLE 18

Nucleic acid sequence alteration in yeast strains with increased levels of DNA repair proteins

| Yeast Strain* | Hyg3S/ 74NT (μg) | Hyg$^r$ (mean ± SD) | Alteration efficiency (1/10$^5$) | Fold |
|---|---|---|---|---|
| LSY678(wt)/pYN132 | 5 | 1811.25 ± 162.76 | 8.26 ± 1.46 | 1× |
| LSY678(wt)/pYNRAD51 | 5 | 2882.75 ± 248.16 | 16.67 ± 6.70 | 2.0× |
| LSY678(wt)/pYNRAD52 | 5 | 143.75 ± 61.45 | 0.54 ± 0.22 | 0.065× |
| LSY678(wt)/pYNRAD54 | 5 | 1952.25 ± 599.96 | 12.11 ± 5.27 | 1.5× |
| Δrad51/pYN132 | 5 | 72.14 ± 19.37 | 0.56 ± 0.14 | 0.068× |
| Δrad51/pYNRAD51 | 5 | 6164.56 ± 560.03 | 17.60 ± 4.56 | 2.1× |
| Δrad51/pYNRAD52 | 5 | 206.35 ± 65.68 | 0.60 ± 0.36 | 0.073× |
| Δrad51/pYNRAD54 | 5 | 359.51 ± 65.80 | 1.63 ± 0.32 | 0.20× |
| Δrad52/pYN132 | 5 | 339.91 ± 108.99 | 3.65 ± 1.6 | 0.44× |
| Δrad52/pYNRAD51 | 5 | 7646.78 ± 1073.12 | 139.82 ± 49.17 | 17× |
| Δrad52/pYNRAD52 | 5 | 45.53 ± 12.07 | 0.16 ± 0.06 | 0.019× |
| Δrad52/pYNRAD54 | 5 | 2502.67 ± 933.95 | 17.81 ± 6.68 | 2.2× |
| Δrad54/pYN132 | 5 | 262.37 ± 86.74 | 2.16 ± 0.70 | 0.26× |
| Δrad54/pYNRAD51 | 5 | 408.39 ± 55.27 | 2.65 ± 0.85 | 0.32× |
| Δrad54/pYNRAD52 | 5 | 416.47 ± 170.29 | 0.83 ± 0.17 | 0.10× |
| Δrad54/pYNRAD54 | 5 | 840.35 ± 41.65 | 6.04 ± 1.90 | 0.73× |

*All strains also contain pAURHyg(ins)eGFP as the target for alteration. All yeast strains are wild type except for a single mutation in the indicated DNA repair protein and contain plasmids expressing wild-type DNA repair proteins as indicated. The mutations used in these experiments are generally knockout mutations. The results shown are the averages from five experiments.

TABLE 19

Chromosomal alteration in yeast strains with increased levels of DNA repair proteins

| Plasmid in Yeast Strain* | Hyg3S/ 74NT (μg) | Hyg$^r$ | Aur$^r$ (10$^4$) | Alteration efficiency (1/10$^5$) | Fold |
|---|---|---|---|---|---|
| pYN132 | 5 | 2,743 | 519 | 5.28 | 1× |
| pYNRAD51 | 5 | 14,412 | 389 | 37.04 | 7.01× |
| pYNRAD52 | 5 | 2,579 | 531 | 4.86 | 0.92× |
| pYNRAD54 | 5 | 15,028 | 402 | 37.38 | 7.08× |
| pYNRAD51 + pYNRAD54 | 5 | 2,961 | 326 | 9.08 | 1.72× |
| pYNRAD51 + pYNRAD52 | 5 | 2,578 | 359 | 7.18 | 1.36× |
| pYNMRE11 | 5 | 9,451 | 452 | 20.91 | 3.96× |
| pYNXRS2 | 5 | 7,120 | 290 | 24.55 | 4.65× |
| pYNMRE11 + pYNXRS2 | 5 | 23,669 | 409 | 57.87 | 10.96× |

*All strains contain an integrated pAUR101-HYG(rep)eGFP as the target for alteration. All yeast strains are wild type except for the integrated plasmid and contain plasmids expressing wild-type DNA repair proteins as indicated.

TABLE 20

Electrocompetence of LSY678 wild type, Δrad51, Δrad52 and Δrad54

| Yeast Strain* | $^{32}$P (c.p.m.) | Cell density (×10$^7$/ml) | $^{32}$P (c.p.m./10$^8$ cells) | Relative radioactivity |
|---|---|---|---|---|
| LSY678 | 580758.8 | 1.35 | 430191.7 | 1 |
| Δrad51 | 577503.4 | 1.35 | 427780.3 | 0.99 |
| Δrad52 | 600765.9 | 1.38 | 435337.6 | 1.01 |
| Δrad52 | 372718.1 | 1.52 | 245209.3 | 0.57 |

*Strains are electroporated with 4 μM [$^{32}$P]74mer oligonucleotides (5 μl); the cell-associated radioactivity measured after washing is shown. Radioactivity is measured with an LS6500 scintillation counter.

EXAMPLE 3

Cultured Cell Manipulation

Mononuclear cells are isolated from human umbilical cord blood of normal donors using Ficoll Hypaque (Pharmacia Biotech, Uppsala, Sweden) density centrifugation. CD34+ cells are immunomagnetically purified from mononuclear cells using either the progenitor or Multisort Kits (Miltenyi Biotec, Auburn, Calif.). Lin$^-$CD38$^-$ cells are purified from the mononuclear cells using negative selection with StemSep system according to the manufacturer's protocol (Stem Cell Technologies, Vancouver, Calif.). Cells used for microinjection are either freshly isolated or cryopreserved and cultured in Stem Medium (S Medium) for 2 to 5 days prior to microinjection. S Medium contains Iscoves' Modified Dulbecco's Medium without phenol red (IMDM) with 100 μg/ml glutamine/penicillin/streptomycin, 50 mg/ml bovine serum albumin, 50 μg/ml bovine pancreatic insulin, 1 mg/ml human transferrin, and IMDM; Stem Cell Technologies), 40 μg/ml low-density lipoprotein (LDL; Sigma, St. Louis, Mo.), 50 mM HEPEs buffer and 50 μM 2-mercaptoethanol, 20 ng/ml each of thrombopoietin, flt-3 ligand, stem cell factor and human IL-6 (Pepro Tech Inc., Rocky Hill, N.J.). After microinjection, cells are detached and transferred in bulk into wells of 48 well plates for culturing.

35 mm dishes are coated overnight at 4° C. with 50 μg/ml Fibronectin (FN) fragment CH-296 (Retronectin; TaKaRa Biomedicals, Panvera, Madison, Wis.) in phosphate buffered saline and washed with IMDM containing glutamine/penicillin/streptomycin. 300 to 2000 cells are added to cloning rings and attached to the plates for 45 minutes at 37° C. prior to microinjection. After incubation, cloning rings are removed and 2 ml of S Medium are added to each dish for microinjection. Pulled injection needles with a range of 0.22μ to 0.3μ outer tip diameter are used. Cells are visualized with a microscope equipped with a temperature controlled stage set at 37° C. and injected using an electronically interfaced Eppendorf Micromanipulator and Transjector. Successfully injected cells are intact, alive and remain attached to the plate post injection. Molecules that are flourescently labeled allow determination of the amount of oligonucleotide delivered to the cells.

For in vitro erythropoiesis from Lin$^-$CD38$^-$ cells, the procedure of Malik, 1998 can be used. Cells are cultured in ME Medium for 4 days and then cultured in E Medium for 3 weeks. Erythropoiesis is evident by glycophorin A expression as well as the presence of red color representing the presence of hemoglobin in the cultured cells. The injected cells are able to retain their proliferative capacity and the ability to generate myeloid and erythoid progeny. CD34+ cells can convert a normal A ($β^A$) to sickle T ($β^S$) mutation in the β-globin gene or can be altered using any of the oligonucleotides of the invention herein for correction or alteration of a normal gene to a mutant gene. Alternatively, stem cells can be isolated from blood of humans having genetic disease mutations and the oligonucleotides of the invention can be used to correct a defect or to modify genomes within those cells.

Alternatively, non-stem cell populations of cultured cells can be manipulated using any method known to those of skill in the art including, for example, the use of polycations, cationic lipids, liposomes, polyethylenimine (PEI), electroporation, biolistics, calcium phophate precipitation, or any other method known in the art.

As with the cells in the other compositions and methods of the invention, the cells used in this example have increased levels or activity of at least one of the RAD10, RAD51, RAD52, RAD54, RAD55, MRE11, PMS1 or XRS2 proteins and/or decreased levels or activity of at least one protein selected from the group consisting of RAD1, RAD51, RAD52, RAD57 or PMS1. The cells may naturally have such increased or decreased levels or activity, e.g. the cells comprise a mutation that confers such an increase or decrease, or the levels or activity may be increased or decreased using any method described elsewhere herein. Such methods include, but are not limited to, increasing levels or activity by transiently or permanently transfecting the cells with at least one gene encoding one of the proteins; adding a compound that stimulates the expression of at least one gene or that stimulates the activity of at least one protein; or decreasing levels or activity of at least one protein selected from the group consisting of RAD1, RAD51, RAD52, RAD57 or PMS1 by antisense or other methods.

EXAMPLE 4

Treatment of Blood Disorders

The compositions and methods of the invention can be used, for example, in therapeutic approaches when the target cell is a stem cell. These approaches can be used with a variety of pluripotent stem cells, including, for example, any of the 64 stem cell lines in the National Institutes of Health list which are described elsewhere herein, embryonic stem cells, and hematopoietic stem cells. Such an approach with any of these cell types is particularly advantageous because the target cell can be manipulated ex vivo allowing for correction of the mutation and selection of a clone with the desired alteration. The cells are then reintroduced into the patient resulting in repopulation in whole or in part with progeny from the genetically corrected stem cell. For hematopoietic stem cells, the cells are typically reintroduced after the patient's bone marrow has been ablated, although complete eradication of host hematopoiesis is not required to achieve therapeutic effects (see, e.g., Blau, *Baillieres Clin. Haematol* 11:257–275 (1998). Many diseases of blood, such as sickle cell anemia, thallassemias, immunological and clotting disorders, can be treated using the compositions and methods of the invention to correct mutations into the chromosomal DNA of hematopoietic stem cells and transplanting these cells into a patient.

Most therapeutic approaches on stem cells use viral vectors, e.g. retroviral vectors, portions of adenovirus (Ad) or adeno-associated virus (AAV), to deliver nucleic acid sequences encoding partial or complete portions of a particular protein. The protein is expressed in the cell which results in the desired phenotype. See, for example, U.S. Pat. Nos. 5,700,470 and 5,139,941. The use of such transgene vectors in any eukaryotic organism adds one or more exogenous copies of a gene, which gene may be foreign to the host, in a usually random fashion at one or more integration sites of the organism's genome at some frequency. The gene which was originally present in the genome, which may be a normal allelic variant, mutated, defective, and/or functional, is retained in the genome of the host.

Treatment of sickle cell disease. As a model for the correction of mutations in stem cells using the compositions and methods of the invention, we test their ability to correct the hemoglobin sickle mutation in mice. Numerous transgenic mouse strains have been developed which exclusively express human globins, including the sickle allele. Mice that exclusively express human sickle hemoglobin exhibit significant sickle pathology which is sufficiently faithful to test antisickling treatments regimens. See, for example, Blouin et al., Blood 94:1451–1459 (1999) and Fabry et al., Blood 97:410–418 (2001). In addition, methods for purifying and culturing hematopoietic stem cells are well known to one of ordinary skill in the art. See, for example, Spangrude et al., Science 214:58–62 (1988) and U.S. Pat. No. 6,261,841.

We purify hematopoietic stem cells from mice, correct the sickle allele, reintroduce into mice and monitor sickling phenotype.

As described for the cells in Example 3, the cells used in this example have increased levels or activity of at least one of the RAD10, RAD51, RAD52, RAD54, RAD55, MRE11, PMS1 or XRS2 proteins and/or decreased levels or activity of at least one protein selected from the group consisting of RAD1, RAD51, RAD52, RAD57 or PMS1. The cells may naturally have such increased or decreased levels or activity, e.g. cells comprising a mutation that confers such an increase or decrease. The presence of such a mutation or mutations may be detected by methods known in the art including, but not limited to, base-specific primer extension, allele-specific PCR, and hybridization to microarrays. See also, for example, International Patent Application of University of Delaware entitled "Polymorphism Detection and Separation," filed concurrently herewith. In addition, the levels or activity may be increased or decreased using any method described elsewhere herein.

Although a number of embodiments and features have been described above, it will be understood by those skilled in the art that modification and variations of the described embodiments and features may be made without departing from either the spirit of the invention or the scope of the appended claims. The publications and patents cited herein are incorporated by reference in their entireties.

What is claimed is:

1. A method of oligonucleotide-mediated nucleic acid sequence alteration comprising:
   providing an altered cell or cell-free extract comprising a target nucleic acid sequence, wherein the altered cell or cell-free extract has been altered such that it exhibits increased expression or protein activity relative to unaltered cell or cell-free extract of at least one protein selected from the group consisting of RAD10, RAD51, RAD52, RAD54, RAD55, MRE11, PMS1, XRS2, and combinations thereof, and further wherein said altered cell or cell-free extract exhibits decreased expression or protein activity relative to unaltered cell or cell-free extract of at least one other protein selected from the group consisting of RAD10, RAD51, RAD52, RAD54, RAD55, MRE11, PMS1, XRS2, and combinations thereof;
   providing an oligonucleotide adapted for altering at least one nucleotide in said target nucleic acid sequence; and
   introducing said oligonucleotide to the cell or cell-free extract under suitable conditions to allow recombination with the target nucleic acid sequence.

2. The method of claim 1 in which the nucleic acid sequence alteration is a deletion, insertion or replacement alteration.

3. The method of claim 1, wherein the decrease in expression or protein activity of at least one other protein comprises a mutation in a gene encoding the protein.

4. The method of claim 1, wherein the decrease in expression or protein activity of at least one protein comprises addition of an inhibitor of the activity or the expression of a target protein or nucleic acid target sequence.

5. The method of claim 1, wherein the nucleic acid sequence alteration affects 1, 2, or 3 consecutive nucleotides in the target nucleic sequence.

6. The method of claim 1, wherein the oligonucleotide binds to the non-transcribed strand of a gene at a target site.

7. The method of claim 1, wherein the oligonucleotide is a chimeric, RNA-DNA, double-hairpin oligonucleotide or a modified single-stranded oligonucleotide.

8. The method of claim 1, wherein the nucleic acid sequence alteration is in a target nucleic acid selected from the group consisting of: plasmids, cosmids, artificial chromosomes, YACs, BAGs, PLACs, and BiBACs.

9. The method of claim 1, wherein the cell is selected from a fungal, plant, animal, mammal or human cell.

10. The method of claim 1, wherein the cell-free extract is from a fungal, plant, animal, mammal or human cell source.

* * * * *